(12) United States Patent
Love et al.

(10) Patent No.: US 9,244,080 B2
(45) Date of Patent: Jan. 26, 2016

(54) METHOD FOR DIAGNOSING ALLERGIC REACTIONS

(75) Inventors: J. Christopher Love, Somerville, MA (US); Qing Han, Cambridge, MA (US); Vinay Tripuraneni, Durham, NC (US)

(73) Assignee: Massachussetts Institute of Technology, Cambridge, MA (US)

( * ) Notice: Subject to any disclaimer, the term of this patent is extended or adjusted under 35 U.S.C. 154(b) by 93 days.

(21) Appl. No.: 13/132,858

(22) PCT Filed: Dec. 4, 2009

(86) PCT No.: PCT/US2009/066876
§ 371 (c)(1),
(2), (4) Date: Sep. 7, 2011

(87) PCT Pub. No.: WO2010/065929
PCT Pub. Date: Jun. 10, 2010

(65) Prior Publication Data
US 2012/0015824 A1    Jan. 19, 2012

Related U.S. Application Data

(60) Provisional application No. 61/120,033, filed on Dec. 4, 2008.

(51) Int. Cl.
*G01N 33/53* (2006.01)
*B82Y 30/00* (2011.01)
*B01L 3/00* (2006.01)
*G01N 33/531* (2006.01)
*G01N 21/64* (2006.01)
*G01N 33/543* (2006.01)
*G01N 33/68* (2006.01)
*G01N 33/577* (2006.01)
*G01N 33/50* (2006.01)

(52) U.S. Cl.
CPC ........ *G01N 33/6863* (2013.01); *G01N 33/5047* (2013.01); *G01N 33/54366* (2013.01); *G01N 33/6854* (2013.01)

(58) Field of Classification Search
CPC .............................. C40B 20/02; C40B 20/04
See application file for complete search history.

(56) References Cited

U.S. PATENT DOCUMENTS

| 4,729,949 A | 3/1988 | Weinreb et al. |
| 6,210,910 B1 | 4/2001 | Walt et al. |
| 6,377,721 B1 | 4/2002 | Walt et al. |

(Continued)

FOREIGN PATENT DOCUMENTS

| CN | 102308213 A | 1/2012 |
| EP | 2370814 A2 | 10/2011 |

(Continued)

OTHER PUBLICATIONS

Bradshaw et al., "Concurrent detection of secreted products from human lymphocytes by microengraving: Cytokines and antigen-reactive antibodies", *Clinical Immunology*, 129(1):10-18 (2008).

(Continued)

*Primary Examiner* — Cherie M Stanfield
(74) *Attorney, Agent, or Firm* — Choate, Hall & Stewart, LLP

(57) ABSTRACT

The invention provides a method for multiple cytokine detection from single cells for the purpose of generating immunological profiles of diseases.

34 Claims, 25 Drawing Sheets

(56) References Cited

U.S. PATENT DOCUMENTS

| | | | |
|---|---|---|---|
| 6,410,252 | B1 | 6/2002 | Lehmann et al. |
| 7,776,553 | B2 * | 8/2010 | Love et al. ............... 435/7.1 |
| 2010/0255471 | A1 | 10/2010 | Clarke et al. |
| 2011/0111981 | A1 | 5/2011 | Love et al. |

FOREIGN PATENT DOCUMENTS

| | | | |
|---|---|---|---|
| JP | H08-259598 | A | 10/1996 |
| JP | 2003-531377 | A | 10/2003 |
| JP | 2004-528546 | A | 9/2004 |
| JP | 2009-520029 | A | 5/2009 |
| JP | 2012-511155 | A | 5/2012 |
| WO | WO-01/79843 | A2 | 10/2001 |
| WO | WO-02/073195 | A2 | 9/2002 |
| WO | WO-02/078844 | A1 | 10/2002 |
| WO | WO-03035824 | A1 | 5/2003 |
| WO | WO-2007035633 | A2 | 3/2007 |
| WO | WO 2007035633 | A2 * | 3/2007 |
| WO | WO-2007/075605 | A2 | 7/2007 |
| WO | WO-2008/135196 | A1 | 11/2008 |
| WO | WO-2009/145925 | A1 | 12/2009 |
| WO | WO-2010/065929 | A2 | 6/2010 |
| WO | WO-2010/085275 | A1 | 7/2010 |
| WO | WO-2010/096652 | A1 | 8/2010 |

OTHER PUBLICATIONS

Love J C et al., "A microengraving method for rapid selection of single cells producing antigen-specific antibodies" *Nature BioTechnology*, 24(6):703-707 (2006).

Kent et al., "Enumeration and Phenotype of Autoreactive B Cells in Pancreatic Draining Lymph Nodes from Type 1 Diabetes Subjects", *Clinical Immunology*, 131(1): S19 (2009).

Harriman et al., "Antibody discovery via multiplexed single cell characterization", *Journal of Immunological Methods*, 341:135-145 (2009).

Haining, W. Nicholas, Travels in time: Assessing the functional complexity of T cells, PNAS, 109(5):1359-1360 (2012).

Han et al., Polyfunctional responses by human T cells result from sequential release of cytokines, PNAS, 105(5):1607-1612 (2012).

Han et al., Polyfunctional responses by human T cells result from sequential release of cytokines, Supporting information to PNAS, 105(5):1607-1612 (2012) published on-line (11 pages).

Beer et al., On-Chip Single-Copy Real-Time Reverse-Transcription PCR in Isolated Picoliter Droplets, Analytical Chemistry, 80(6): 1854-1858 (2008).

Chen, H.J.H. et al., A Novel Micro-Well Array Chip for Liquid Phase Biomaterial Processing and Detection, Sensors and Actuators, 108:193-200 (2003).

Communication pursuant to Article 94(3) EPC for EP09799214.3, 4 pages (Nov. 5, 2013).

First Office Action for CN200980156181.4, 11 pages (Jul. 5, 2013).

International Search Report for PCT/US2009/066876, 3 pages (Jul. 20, 2010).

Khattri, et al., An Essential Role for Scurfin in CD4 CD25 T Regulatory Cells, Nature Immunology, 4(4): 337-342 (2003).

Notice of Reasons for Rejection for JP2011539763, 2 pages (Nov. 13, 2013).

Official Action for IL213206, 5 pages (Jul. 22, 2013).

Opposition against European Patent No. 1566635, 28 pages (Sep. 7, 2012).

Ostuni, E. et al., Selective Deposition of Proteins and Cells in Arrays of Microwells, Langmuir, 17:2828-2834 (2001).

Reply to Opposition against European Patent No. 1566635, 25 pages (Apr. 29, 2013).

Sasuga, Y. et al., Single-Cell Chemical Lysis Method for Analyses of Intracellular Molecules Using an Array of Picoliter-Scale Microwells, Analytical Chemistry, 80:9141-9149 (2008).

Schutten, et al., Development of a Real-Time Quantitative RT-PCR for the Detection of HIV-2 RNA in Plasma, Journal of Vircological Methods 88:81-87 (2000).

Warren, et al., Transcription Factor Profiling in Individual Hematopoietic Progenitors by Digital RT-PCR, PNAS, 103 (47): 17807-17812 (2006).

Written Opinion for PCT/US2009/066876, Jul. 20, 2010 (5 pages).

Written Opinion for SG 201104033-4, 8 pages (Sep. 24, 2012).

Steenbakkers, et al., A New Approach to the Generation of Human or Murine Antibody Producing Hybridomas, Journal Immunological Methods, 152: 69-77 (1992).

Abbas et al., Cellular and Molecular Immunology, 2nd Ed.: 92-93 (1994).

Clark et al., Regulation of Human B-Cell Activation and Adhesion, Annual Review Immunology, 9: 97-127 (1991).

Muraguchi et al., Microwell Array Chip for Detecting Antigen-Specific Lymphocytes and Method for Detecting Antigen-Specific Lymphocytes, English Translation of Japanese Patent Application No. 2002-331031, (filed Nov. 14, 2002).

Muraguchi et al., Method for Cloning Antigen-Specific Lymphocyte Antigen Receptor Gene, English Translation of Japanese Patent Application No. 2002-346728, (filed Nov. 29, 2002).

Alberts, B. et al., Looking at the Structure of Cells in the Microscope, Molecular Biology of the Cell, 4:551 (2002).

Bailey, J.R. et al., Residual human immunodeficiency virus type 1 viremia in some patients on antiretroviral therapy is dominated by a small number of invariant clones rarely found in circulating CD4+ T cells, J. Virol., 80(13):6441-57 (2006).

Beer, N. R. et al., On-chip, real-time, single-copy polymerase chain reaction in picoliter droplets, Anal. Chem., 79(22):8471-5 (2007).

Bengtsson, M. et al., Quantification of mRNA in single cells and modelling of RT-qPCR induced noise, BMC Mol. Biol., 9:63 (2008).

Carpenter, A.E. et al., CellProfiler: image analysis software for identifying and quantifying cell phenotypes, Genome Biol. 7(10):R100 (2006).

Chen, C. et al. Real-time quantification of microRNAs by stem-loop RT-PCR, Nucleic Acids Res., 33(20):e179 (2005).

Chun, T.W. et al., In vivo fate of HIV-1-infected T cells: quantitative analysis of the transition to stable latency, Nat. Med., 1(12):1284-90 (1995).

Chun, T.W. et al., Presence of an inducible HIV-1 latent reservoir during highly active antiretroviral therapy, Proc. Natl. Acad. Sci. U S A, 94(24):13193-7 (1997).

Chun, T.W. et al., Quantification of latent tissue reservoirs and total body viral load in HIV-1 infection, Nature, 387(6629):183-8 (1997).

Deeks, S.G. et al., Virologic and immunologic consequences of discontinuing combination antiretroviral-drug therapy in HIV-infected patients with detectable viremia, N. Engl. J. Med., 344(7):472-80 (2001).

DiCarlo, D. and Lee, L.P., Dynamic single-cell analysis for quantitative biology, Anal. Chem., 78(23):7918-25 (2006).

Diehl, F. et al., BEAMing: single-molecule PCR on microparticles in water-in-oil emulsions, Nat. Methods., 3(7):551-9 (2006).

Embleton, M.J. et al., In-cell PCR from mRNA: amplifying and linking the rearranged immunoglobulin heavy and light chain V-genes within single cells, Nucleic Acids Res., 20(15):3831-7 (1992).

Embretson, J. et al., Analysis of human immunodeficiency virus-infected tissues by amplification and in situ hybridization reveals latent and permissive infections at single-cell resolution, Proc. Natl. Acad. Sci. U S A., 90(1):357-61 (1993).

Engvall, E. and Perlmann, P., 3. Quantitation of specific antibodies by enzyme-labeled anti-immunoglobulin in antigen-coated tubes, J. Immunol., 109(1):129-35 (1972).

Finzi D. et al., Latent infection of CD4+ T cells provides a mechanism for lifelong persistence of HIV-1, even in patients on effective combination therapy, Nat. Med., 5(5):512-7 (1999).

Finzi, D. et al., Identification of a reservoir for HIV-1 in patients on highly active antiretroviral therapy, Science, 278(5341):1295-300 (1997).

Han, Q. et al., Multidimensional analysis of the frequencies and rates of cytokine secretion from single cells by quantitative microengraving, Lab Chip, 10(11):1391-400 (2010).

Han, Y. et al., Experimental approaches to the study of HIV-1 latency, Nat. Rev. Microbiol., 5(2):95-106 (2007).

(56) References Cited

OTHER PUBLICATIONS

Han, Y. et al., Resting CD4+ T cells from human immunodeficiency virus type 1 (HIV-1)-infected individuals carry integrated HIV-1 genomes within actively transcribed host genes, J. Virol., 78(12):6122-33 (2004).

Hermankova, M. et al., Analysis of human immunodeficiency virus type 1 gene expression in latently infected resting CD4+ T lymphocytes in vivo, J. Virol., 77(13):7383-92 (2003).

Holland, P.M. et al., Detection of specific polymerase chain reaction product by utilizing the 5'—3' exonuclease activity of Thermus aquaticus DNA polymerase, Proc. Natl. Acad. Sci. U S A., 88(16):7276-80 (1991).

Kiss, M.M. et al., High-throughput quantitative polymerase chain reaction in picoliter droplets, Anal. Chem., 80(23):8975-81 (2008).

Kumaresan, et al., High-throughput single copy DNA amplification and cell analysis in engineered nanliter droplets, Analytical Chemistry, 80:3522-3529 (2008).

Lassen, K.G. et al., Analysis of human immunodeficiency virus type 1 transcriptional elongation in resting CD4+ T cells in vivo, J. Virol., 78(17):9105-14 (2004).

Lassen, K.G. et al., Nuclear retention of multiply spliced HIV-1 RNA in resting CD4+ T cells, PLoS Pathog., 2(7):e68 (2006).

Leamon, J.H. et al., A massively parallel PicoTiterPlate based platform for discrete picoliter-scale polymerase chain reactions, Electrophoresis, 24(21):3769-77 (2003).

Lindström, S. et al., PCR amplification and genetic analysis in a microwell cell culturing chip, Lab Chip, 9(24):3465-71 (2009).

Liss, B., Improved quantitative real-time RT-PCR for expression profiling of individual cells, Nucleic Acids Res., 30(17):e89 (2002).

Malnati, M.S. et al., A universal real-time PCR assay for the quantification of group-M HIV-1 proviral load, Nat. Protoc., 3(7):1240-8 (2008).

Marcus, J.S. et al., Microfluidic single-cell mRNA isolation and analysis, Anal. Chem., 78(9):3084-9 (2006).

Marcus, J.S. et al., Parallel picoliter rt-PCR assays using microfluidics, Anal. Chem., 78(3):956-8 (2006).

Margulies, M. et al., Genome sequencing in microfabricated high-density picolitre reactors, Nature, 437(7057):376-80 (2005).

Mazutis, L. et al., Droplet-based microfluidic systems for high-throughput single DNA molecule isothermal amplification and analysis, Anal. Chem., 81(12):4813-21 (2009).

Meijer, P.J. et al., Isolation of human antibody repertoires with preservation of the natural heavy and light chain pairing, J. Mol. Biol., 358(3):764-72 (2006).

Monie, D. et al., A novel assay allows genotyping of the latent reservoir for human immunodeficiency virus type 1 in the resting CD4+ T cells of viremic patients, J. Virol., 79(8):5185-202 (2005).

Nagai, H. et al., Development of a microchamber array for picoliter PCR, Anal. Chem., 73(5):1043-7 (2001).

No Author Listed, Executive summary, 2008 Report on the global AIDS epidemic, Joint United Nations Programme on HIV/AIDS (UNAIDS), 36 pages (2008).

Ogunniyi, A.O. et al., Screening individual hybridomas by microengraving to discover monoclonal antibodies, Nat. Protoc., 4(5):767-82 (2009).

Persaud, D. et al., A stable latent reservoir for HIV-1 in resting CD4(+) T lymphocytes in infected children, J. Clin. Invest., 105(7):995-1003 (2000).

Schacker, T. et al., Rapid accumulation of human immunodeficiency virus (HIV) in lymphatic tissue reservoirs during acute and early HIV infection: implications for timing of antiretroviral therapy, J. Infect. Dis., 181(1):354-7 (2000).

Toriello, N. M. et al., Integrated microfluidic bioprocessor for single-cell gene expression analysis, Proc. Natl. Acad. Sci. U S A., 105(51):20173-8 (2008).

Van Duin, J. and Tsareva, N., Single-Stranded RNA Phages, The Bacteriophages, 2(15):175-196 (2006).

Wang, X. and Stollar, B.D., Human immunoglobulin variable region gene analysis by single cell RT-PCR, J. Immunol. Methods., 244(1-2):217-25 (2000).

Warbrick, E.V. et al. Induced changes in total serum IgE concentration in the Brown Norway rat: potential for identification of chemical respiratory allergens, J. Appl. Toxicol., 22(1):1-11 (2002).

Warren, L., Single-Cell Gene-Expression Analysis by Quanitative RT-PCR, California Institute of Technology, 1-225 (2008).

Wong, J.K. et al., Recovery of replication-competent HIV despite prolonged suppression of plasma viremia, Science, 278(5341):1291-5 (1997).

Yamamura, S. et al., Single-cell microarray for analyzing cellular response, Anal. Chem., 77(24):8050-6 (2005).

Yu, X. et al., Neutralizing antibodies derived from the B cells of 1918 influenza pandemic survivors, Nature, 455(7212):532-6 (2008).

Zhang, K. et al., Sequencing genomes from single cells by polymerase cloning, Nat. Biotechnol., 24(6):680-6 (2006).

Zhou, Y et al., Kinetics of human immunodeficiency virus type 1 decay following entry into resting CD4+ T cells, J. Virol., 79(4):2199-210 (2005).

Zhu, T. et al., Evidence for human immunodeficiency virus type 1 replication in vivo in CD14(+) monocytes and its potential role as a source of virus in patients on highly active antiretroviral therapy, J. Virol., 76(2):707-16 (2002).

\* cited by examiner

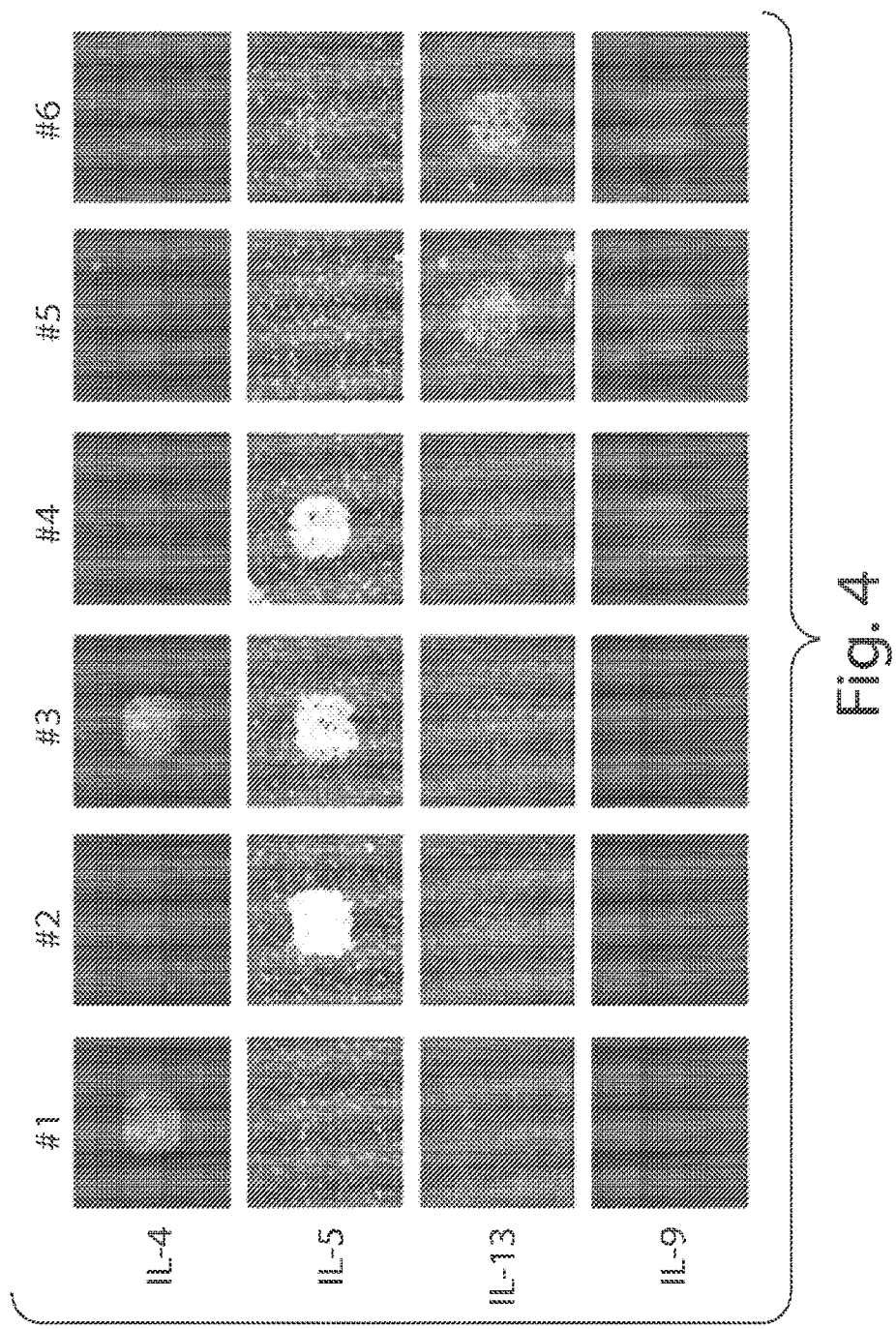

The Problem
Current Allergy Testing

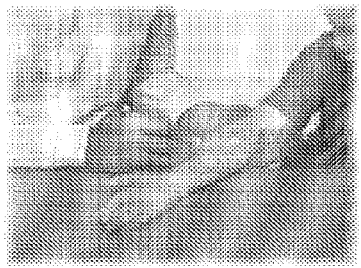

Percutaneous (Skin Prick) Testing

The blood test measures the levels of allergy antibody, or IgE, produced when your blood is mixed with a series of allergens in a laboratory

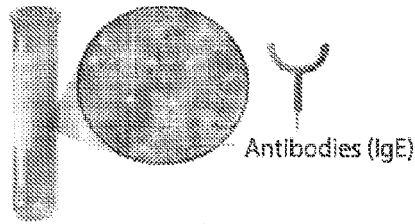

Sera testing for IgE (RAST or ELISA)

Skin testing
- Multiple pin pricks with panel of allergens
- Measures short-term and long-term immune responses
- *Qualitative* assessment of superficial inflammation
- *Traumatic experience* for infants and parents
- Often, *single data point* in child's history

Immunosorbent assays
- Minimally invasive blood draw (5 mL sample)
- Measures serum titers of IgE antibodies
- *Complicated* by pan-specificity of antibodies and elevated levels from other conditions (HIV, skin disease, parasites)
- *Not predictive*—single parameter
- Correlation over time challenging

Food Challenge
- Double blind test with various foods (some that are suspected of inducing a reaction) are given to patient
- Cannot be used on patients with history of severe (anaphylactic) reactions

The serum sample is incubated with an allergen disc. During this step,IgE molecules with specificities for the various allergenic components bind to the allergen disc.

Proteins non-specifically bound are washed away with a buffer containing detergent. Only specifically bound IgE remains on the disc.

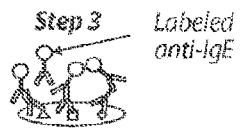

The disc is incubated with labeled anti-human IgE antibody, which binds specifically to the IgE on the disc. The amount of labeled antibody bound is directly proportional to the amount of IgE present on the disc.

Unbound antibody is washed away with buffer containing detergent.

Specific IgE is quantitated either through the reaction of labeled antibody with an enzyme substrate (EIA), or by counting radioactivity (RAST).

Fig. 17-1

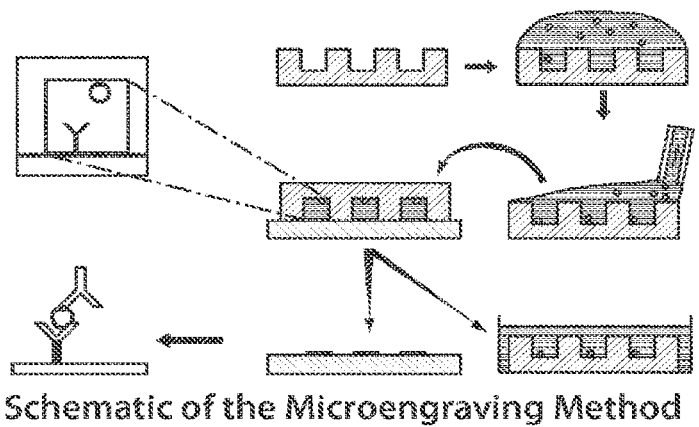

FIG. 18A

How it Works
• Cells, suspended in media, are deposited onto a large array of microwells molded on a poly (dimethylsiloxane) slab, and allowed to settle from suspension in the microwells at a density of ~1 cell.well.

• The loaded microwells are then inverted onto a glass slide coated with a specific capture reagent (e.g., anti-cytokine).

• After an incubation period, the microwells are removed and applied to a second glass slide coated with a different capture reagent (e.g., anti-IgG and anti-IgM).

• The resulting microarrays are interrogated with fluorescently labeled reagents for detection and laser-based fluorescence scanners.
• After printing, the cells in the wells can be stained *in situ* for subsequent imaging by immunofluorescence.

FIG. 18B

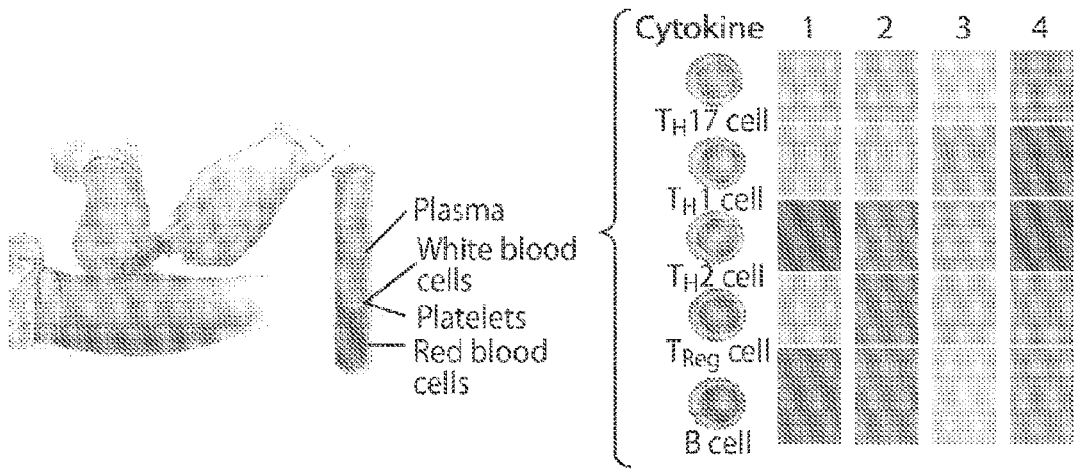

FIG. 19A

Elucidating the Unique Immunological Profile of an Allergic Individual

- Whole blood from a patient is drawn, and cells of interest are isolated.
- Cells are stimulated with allergens and are used for microengraving.
- The resulting cellular microarray is read as an "allergy-array" which provides specific data concerning reactivity to the allergen(s) of interest.

Advantages of this Diagnostic:
- Small blood volumes are needed for a comprehensive allergic profile, so pediatric/infant allergy testing is possible.
- Diagnostics are performed over time to assess a patients reactivity over time, as well as potentially measure the efficacy of immunotherapy.
- Data from the "allergy-array" are used to predict cross-reactivity to related allergens.

FIG. 19B

METHOD FOR DIAGNOSING ALLERGIC REACTIONS

RELATED APPLICATIONS

This application is a national stage application, filed under 35 U.S.C. §371, of International Application No. PCT/US2009/066876, filed Dec. 4, 2009, which claims the benefit of provisional application, U.S. Ser. No. 61/120,033, filed Dec. 4, 2008, the contents of which are herein incorporated by reference in their entirety.

STATEMENT AS TO FEDERALLY SPONSORED RESEARCH

This invention was funded in part by the U.S. Government under grant number 5U19AI050864-07, awarded by the National Institutes of Health. The Government has certain rights in the invention.

FIELD OF THE INVENTION

The invention provides methods for detecting multiple cytokines and correlated surface-expressed immunophenotypic biomarkers from single cells for the purpose of generating immunological profiles of diseases.

BACKGROUND OF THE INVENTION

It is well known that individual cells, even those identical in appearance, differ in numerous characteristics, such as variability in the expression of a particular gene, concentration of a critical metabolite or ion, or pattern of response to a given stimulus. Living cells possess very low copy numbers of many components, including deoxyribonucleic acid (DNA) and important regulatory molecules. Both stochastic events inherent in the biochemical process of gene expression (intrinsic noise) and fluctuations in other cellular components (extrinsic noise) contribute substantially to overall variation among cells. Cell types, mutations, and fluctuations all contribute to the diversity of cells in the body.

However, most clinical or cell-based assays analyze cells in bulk, using serum or cell culture media. These assays often average the information over the whole cell population and do not provide detailed information that is critical to evaluate the state of biological system, such as 1) whether two or more genes are co-expressed in the same cell or in different subpopulations of the cells; 2) whether a small increase in expression measured in the ensemble results from a small, homogeneous increase across all cells or a large increase in a subset of cells.

SUMMARY OF THE INVENTION

In a nano- or sub-nanoscale assay system, the methods of the invention provide quantitative measurements of both the frequencies and the distribution in rates of secretion for a plurality (e.g., 2, 4, 5, 6, 8, 10, 20) secreted products, e.g., cytokines, released simultaneously from individual viable cells. The methods provide answers to numerous inquiries in one assay system including: "who" (phenotype or lineage of the interrogated cell), "what" (identity of the secreted product, e.g., cytokine, antibody, chemokine, or growth factor), "how often" (frequency of responders in a population of cells), and "how much" (magnitude of secretion, e.g., level of amount of each secreted product). The methods are useful to profile any secretory cell, e.g., an immune cell such as a T cell or B cell, but are also useful for other secretory cells such as those that secrete hormones or enzymes. The secretory profile of a single viable cell is matched to its phenotype or lineage (e.g., determined by imaging or examination) to yield a secretory profile of the cell. The secretory profile provides valuable information for diagnosis of disease or monitoring of responses to therapeutic intervention.

For example, the invention provides a method for diagnosing an immunological disease in a subject, e.g., infectious disease, autoimmune disease, or allergy. In some embodiments, single cells (or a few cells) are assayed to profile an immunologic response in an individual, e.g., an allergic response. The integrated quantitative (multidimensional) data sets generated using the methods of the invention are used to distinguish responses of cells from different donors to different stimuli. The methods described herein are also useful for clinical monitoring of vaccines, therapeutic biopharmaceuticals, on-going infections, autoimmune diseases, etc.

In one aspect, the invention features a method of determining an immune profile in a subject, e.g., a secreted cytokine profile. The method includes providing a suspension of cells (e.g., live cells) from a subject deposited onto a moldable slab containing at least one microwell (each microwell being less than $100 \times 100 \times 100$ µm$^3$, e.g., $50 \times 50 \times 50$ µm$^3$) in a microwell array, wherein at least one microwell in the microwell array has a single cell subnanoliter volume. In one aspect, the cells are whole blood cells. In another aspect, the cells are peripheral blood mononuclear cells (PBMC). The microwell array is contacted with a substrate, wherein the substrate is pretreated with at least one detection agent (e.g., a cytokine detection agent), and wherein the detection agent binds to a secreted product (e.g., a cytokine) of the cell. In one aspect, the method utilizes at least two detection agents, at least three detection agents, or at least four detection agents. The level of the detection agent on the substrate is measured, wherein the level corresponds to an amount of secreted product of the single cell, thereby detecting the immune profile. Optionally, the detection agent detects a T cell panel of secreted products. In another aspect, the detection agent detects a T-helper 2 (Th$_2$) panel of secreted products.

In one aspect, a rate of secretion is determined for each secreted product. In another aspect, the phenotype of the cell is determined. Optionally, secreted products are matched to surface-expressed markers on cells that distinguish lineages.

A method of determining a profile of an individual viable cell is carried out using the following steps: providing a suspension of cells from a subject deposited onto a moldable slab containing at least one microwell in a microwell array, wherein at least one microwell in the microwell array contains a single cell in a subnanoliter volume; contacting the microwell array with a substrate, wherein the substrate is pretreated with at least one detection agent, and wherein the detection agent binds to a secreted product of said cell to yield a printed microarray; imaging the printed array to yield a dataset; filtering the dataset to identify locations on said array consisting of a single cell; and matching the location with levels of secreted products detected from the single cell locations, thereby determining said immune profile of an individual viable cell. Optionally, the method comprises identifying the phenotype or lineage of single cell and then matching the phenotype or lineage with the level of secreted products at the specified location.

In some embodiments, the profile is a general T cell profile, a Th$_1$ profile, a Th$_2$ profile, a Th$_9$ profile, a Th$_{17}$ profile, or another secretory cell profile. For example, the substrate comprises appropriate pairs of antibodies or a plurality of antibodies to detect cytokines of interest. Exemplary distinct panels of antibodies detecting sets of cytokines indicative of the skewedness of the Th response and specific Th2 and Th1 responses. For example, a general T cell panel detects the following cytokines IL-4/IL-10/IL-17/IFN-γ. An increase in one or more of the cytokines among the secreted products of the interrogated cell indicates its profile. A Th2 panel comprises detection agents for IL-4/IL-5/IL-9. A panel to detect cytotoxic T lymphocyte (CTL) or Th1 profiles comprises detection agents that detect IFNγ/MIP-1β/TNFα/perforin/IL-2, where MIP and/or perforin indicate skewedness toward a CTL phenotype and IL-2 indicate a skewedness toward a Th1 phenotype. A panel comprising detection agents that detect IFNγ/IL-10/IL-17/IL-22 is useful for evaluating mucosal samples, e.g., to determine the immune profile of cells from the gastrointestinal tract (as a mean to evaluate disease/disorder or a predisposition thereto). Detection antibody isotype is useful for evaluating allergies or allergy-prone individuals. For example, panels of detection agents were developed to detect the following panels of antibodies (IgG1/IgA/IgE/IgG4 and IgG1/IgA/IgG3/IgM). Detection of an increase in IgE isotype antibodies indicates an allergic reaction to the stimulating allergen.

A representative Th set includes agents that detect interleukin-17 (IL-17), IL-10, IL-4, interferon-γ (IFN-γ), IL-1b, IL-2, IL-6, IL-7, IL-8, IL-12, IL-21, IL-22, IL-23, macrophage inflammatory protein (MIP) 1b, MIP1a, and/or Interferon-inducible protein (IP)-10. A representative (Th$_2$ set) detects IL-4, IL-5, IL-13 and/or IL-9. In another aspect, the cells are imaged for surface-expressed markers (e.g., CD3, CD4, CD8, CD14, CD19, CD20, CD25, CD27, CD38, CD138, CD95, CD154, CD127). These markers are matched with the cytokine profile for each cell, distinguishing the methods described herein from other previously described capture assays.

The method can alternatively or in addition use a detection agent to detect an antibody, e.g., IgE, IgG$_1$, IgG$_4$, IgGA, IgG$_2$, IgG$_3$, IgM, IgA1, and/or IgA2. A preferred cytokine detection agent is an antibody, e.g., a polyclonal or monoclonal antibody for the cytokine. Alternatively, the cytokine detection agent is an aptamer.

In general, any biological tissue with cytokine-producing cells is used. In some embodiment, peripheral blood mononuclear cells (PBMC) are used. If desired, cells are stimulated prior to depositing cells on the moldable slab. For example, cells are stimulated with a suspected or known allergen. Alternatively, cells are stimulated with peptides, proteins, or intact pathogens from infectious agents.

In some embodiments, the allergen is a food product. For example, the food product is milk, egg, peanut, tree nut, fish, shellfish, soy, wheat, egg products, legumes, or seafood. In some embodiments, the allergen is a drug, e.g., amoxicillin, penicillin, a sulfa drug, a barbiturate, an anticonvulsant, insulin, or iodine. In some embodiments, the allergen is dust, pollen, pet dander, latex, or chlorine, or venom associated with an insect bite, e.g., a bite from a wasp, fire ant or bee sting. In some embodiments, the allergan is a biologic therapeutic, e.g., G-CSF (filgrastim) and GM-CSF (sargramostim), EPO (erythropoietin), RITUXAN® (rituximab), HERCEPTIN® (trastuzumab), human growth hormone, BETASERON® (interferon beta-1b), AVONEX®, (interferon-beta-1a, or ENBREL® (etanercept).

In another aspect, the invention features a method of assessing sensitivity to an allergen in a subject. The method includes providing a suspension of cells from the subject deposited onto a moldable slab containing at least one microwell in a microwell array, wherein at least one microwell in the microwell array has a single cell. Preferably, the cells have been contacted with a test allergen. The microwell array is contacted with a substrate, wherein the substrate is pretreated with at least one detection agent indicative of sensitivity to the allergen. Subsequently, the detection agent is detected, e.g., the level of the detection agent is measured. The level of the detection agent correlates with the level of the secreted product, e.g., cytokine or antibody, thereby assessing sensitivity of the allergen. In one example, detection agent identifies a cytokine, e.g., an increase in the level of a Th2 cytokine, e.g., IL-4, compared to a level of a Th1 cytokine, IFNγ, indicates that subject is allergic or is at risk of developing an allergy to said allergen. In another example, the detection agent detects antibody isotype and increase in IgE isotype compared to other isotypes such as IgG's (in particular, IgG$_4$, IgM, or IgA) indicates an allergic reaction to the stimulating allergen and an allergy or predisposition thereto of the subject from which the cell was obtained.

In another aspect, the invention features a method of determining a cytokine profile in a subject indicative of an autoimmune disease or infectious disease. First, a suspension of cells from a subject deposited onto a moldable slab containing at least one microwell in a microwell array is provided. In one aspect, at least one microwell in the microwell array has a single cell. Next, the microwell array is contacted with a substrate. In one aspect, the substrate is pretreated with at least one cytokine detection agent. Finally, the cytokine detection agent is detected and a cytokine profile indicative of an autoimmune disease or infectious disease is established. An exemplary cytokine profile indicative of an autoimmune disease or infectious disease comprises an increase in a level of IFNγ or IL-2 compared to a normal level of said IFNγ or IL-2.

Exemplary autoimmune diseases include arthritis (including rheumatoid arthritis), multiple sclerosis, immune-mediated or Type 1 diabetes mellitus, inflammatory bowel disease, systemic lupus erythematosus, psoriasis, scleroderma, and autoimmune thyroid diseases. Examples of infectious diseases include, e.g., African trypanosomiasis, cholera, cryptosporidiosis, dengue, hepatitis A, hepatitis B, hepatitis C, HIV/AIDS, influenza, malaria, Japanese encephalitis, malaria, measles, meningitis, onchocerciasis ("river blindness"), pneumonia, rotavirus, schistosomiasis, shigellosis, strep throat, tuberculosis, typhoid, and yellow fever.

In another aspect, a kit is assembled that comprises a substrate, a moldable slab configured to receive the substrate and to provide a fluid tight seal between the moldable slab and the substrate, and instructions for using the conformable support and the substrate to identify species that may associate. The kit preferably has a plurality of microwells and is configured to receive the substrate and to provide a fluid tight seal between the moldable slab and the substrate. The kit preferably includes instructions for using the moldable slab and the substrate to identify species that may associate.

As used herein, the term "associate" refers to interactions such as binding, adsorption, ionic attraction or some other type of interaction between two species. In some examples, species that associate preferably bind to each other with an association constant of at least about $10^9$ $M^{-1}$ or larger. Species which bind to each other with such association constants allow for easy distinction between species that associate and those that do not associate.

In accordance with certain examples, a moldable slab is used in the methods and kits described herein. As used herein "moldable slab" refers to an apparatus which can flex, move or distort, at least in one dimension, when placed in contact with a substrate. For example, in certain configurations the moldable slab may include a material, e.g., an elastomeric material, such that as the moldable slab is placed in contact with a substrate, a substantially fluid tight seal may be formed between the moldable slab and the substrate to retard or to prevent any fluid in the moldable slab from escaping or leaking.

The moldable slab is fabricated by soft lithography and replica molding and is of a biocompatible material, which is not toxic and gas permeable. The moldable slab or the substrate or both comprises one or more materials selected from the group consisting of glass, plastic, polystyrene, polycarbonate, poly(dimethylsiloxane), nitrocellulose, poly(vinylidene fluoride), and a metal. The metal is one or more of gold, palladium, platinum, silver, steel or alloys or mixtures thereof. In some embodiments, the substrate is a glass slide, a plastic slide or a bead, and the moldable slabs contain a microwell array. The moldable slab compresses against the substrate to form a tight, but reversible seal with the substrate. The microwell array comprises a block of wells where a well has a diameter of about 50 μm and a depth of about 50 μm and the wells are separated by about 50 μm or a well has a diameter of about 100 μm and a depth of about 100 μm and the wells are separated by about 100 μm. The wells are sized to retain about 1 nanoliter or less of fluid. Illustrative methods for producing moldable slabs are described in more detail in U.S. Pat. No. 6,180,239 and U.S. Pat. No. 6,776,094, the entire disclosure of each of which is hereby incorporated herein by reference in its entirety.

The exact number of the wells or chambers in the moldable slab may vary. In some examples, the moldable slab includes a single large microwell where a single species may be screened. For example, a moldable slab includes a single type of cell, catalyst or other selected species to be screened. In configurations where the moldable slab is configured as an array, the number of individual microwells may vary from about 1, 4, 8, 24, 48, 96, 384, 1024, 2048, 5096 or more or any value in between these illustrative values.

An engraving plate includes a plurality of wells, each of the wells is less than 100 micrometers in diameter and comprises a single cell. Preferably, the number of cells is less than 5 cells. The engraving plate is a gas-permeable conformable composition. The plate has an elastic modulus (Young's Modulus) in the range of 200-2000 Kilopascal (kPa). The composition of the plate is preferably poly(dimethylsiloxane). The wells of the plate contain at least one cell. That cell is an immune cell, an antibody-producing cell, a hybridoma cell, a T cell, or other cell from the blood or a tissue. The function or secretory profile of the cell or cells is unknown. Optionally, the cell produces a recombinant secreted polypeptide.

In another aspect, the invention provides a test apparatus comprising a moldable slab comprising at least one microwell that forms a microwell array that contacts a substrate with one or more of the cytokine detection agents described herein in a manner to provide a fluid tight seal between the moldable slab and the substrate. The apparatus puts one species, generally a cell, in at least one well of the microwell array. The microwells of the moldable slab are sized and arranged to retain about one nanoliter or less of fluid volume.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

Other features and advantages of the invention are apparent from the following detailed description and claims.

BRIEF DESCRIPTION OF THE DRAWINGS

FIG. 4 is a series of photomicrographs showing quadriplexed Th2 cytokine profiles for CD4+ T cells generated by microengraving.

Figure 1:
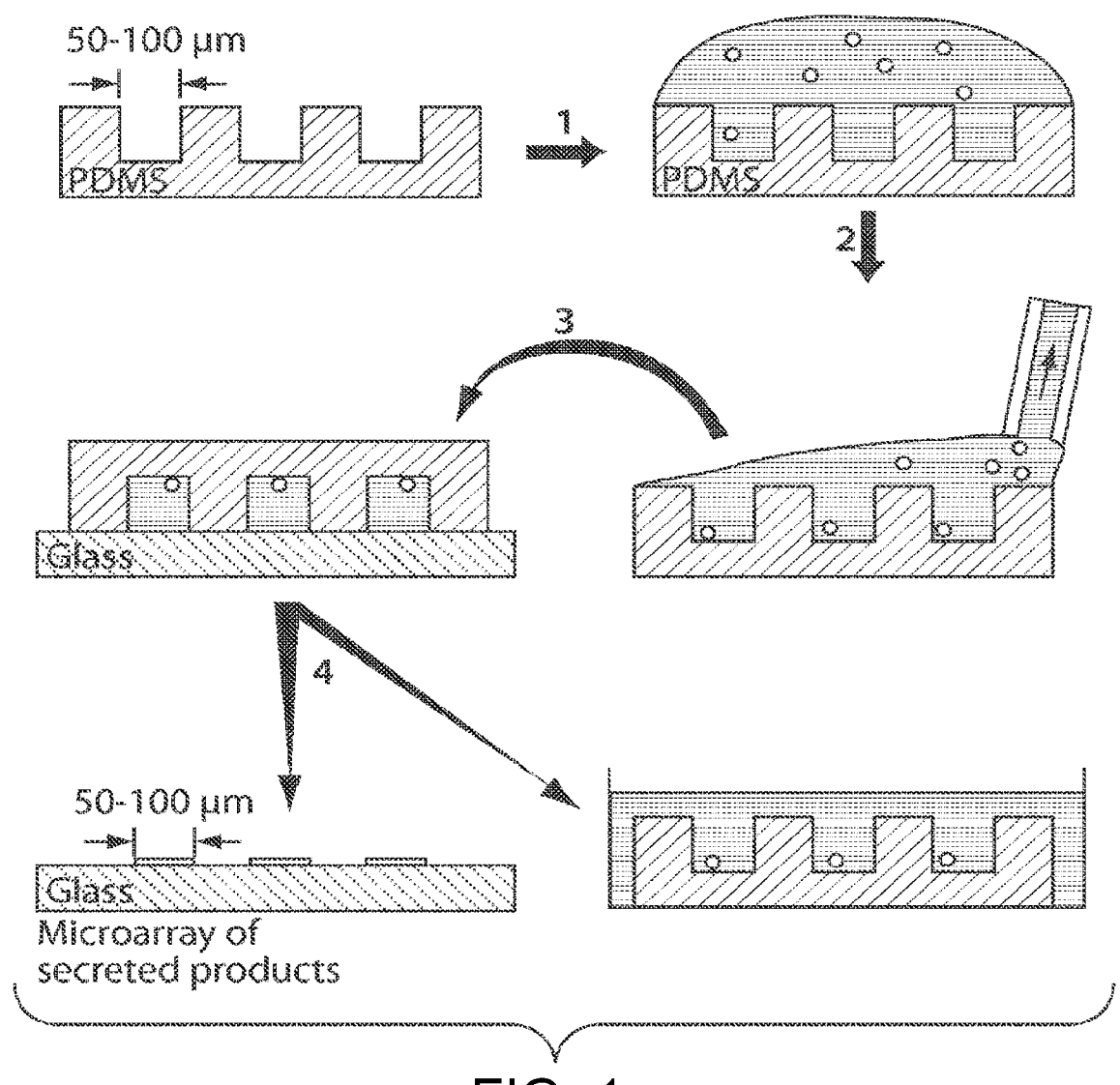
FIG. 1 is a schematic diagram of the procedure for microengraving. (1) A suspension of cells is deposited onto an array of microwells fabricated by soft lithography. (2) The cells are allowed to settle into the wells and then the excess medium is removed by aspiration. (3) The array is placed in contact with a solid support pretreated with capture antibody, compressed lightly, and incubated for 1-2 h. (4) The microwells are removed from the solid support and placed back to the medium. The glass slide is developed by detection antibody.

It will be recognized by the person of ordinary skill in the art, given the benefit of this disclosure, that the examples shown in the figures are not necessarily drawn to scale. Certain features or components may have been enlarged, reduced or distorted to facilitate a better understanding of the illustrative aspects and examples disclosed herein. In addition, the use of shading, patterns, dashes and the like in the figures is not intended to imply or mean any particular material or orientation unless otherwise clear from the context.

DETAILED DESCRIPTION OF THE INVENTION

The invention provides methods of multiplexed cytokine capture. The invention also provides for matching cytokines to surface-expressed markers on cells that distinguish lineages, and quantifying the rates of secretion to enhance the dimensionality of the data. Regions of contact are identified by differential labeling.

Specifically, the invention provides a measure of the frequencies of responding cells following polyclonal mitogens/allergens (e.g., pokeweed mitogen (PWM) and phytohaemagglutinin (PHA)) as well as TCR-specific activation (e.g., anti-CD3/CD28). The rates of secretion are quantified from the collected data. This additional data allows for the assessment of both frequency and magnitude (distribution) of the responses. This additional dimension is important for improving the resolution of the cytokine response. As described below, a specific example involves the measurement of the IL-6 (early inflammatory response marker) secretion from PBMCs from two different donors after stimulation with PWM, PHA, etc. As described below, the frequencies of responding cells is varied, but not matched to the magnitude of the responses. Statistical tests show that the distributions are unique. This multidimensional data improves the quality of immune monitoring of diseases (e.g., allergy, infectious, autoimmune, etc.). These measures are implemented for more than one cytokine (at least four) per cell.

As described below, surface expressed phenotypic markers (e.g., CD4 and CD8) are matched to the individual measures, further refining the resolution of the data to identify unique subsets by imaging cytometry and matched cytokine release. The rates of secretion for different cytokines are correlated for single cells. The methods described herein allow for integrated quantitative (multidimensional) data sets, and the data show that these measures are used to distinguish responses of cells from different donors to different stimuli. The applications of the invention include allergy testing, clinical monitoring of vaccines, therapeutic biopharmaceuticals, on-going infections, autoimmune diseases, etc.

The invention provides methods and compositions for testing an individual's sensitivity to one or more allergens by examining levels of cytokines that are characteristic of an allergic reaction. Allergy is one type of hypersensitivity of the immune system, which is caused by contacting environment substances known as allergens. Allergy is a worldwide epidemic disease. Allergic immune response requires sensitization and development of specific immune response towards allergen. During sensitization to allergen, activation of allergen-specific CD4$^+$ T$_{h2}$ cells results in the production of T$_{h2}$ cytokines (such as IL-4 and IL-13), which are responsible for inducing class switching to IgE in B cells, mucus production, and activation of endothelial cells for T$_{h2}$ cell and eosinophil migration to tissues. IgE sensitizes mast cells and basophils by binding to the high-affinity receptor for IgE (FcεRI) expressed on their surface. On cross-linking of the IgE-FcεRI complexes by allergen, mast cells and basophils degranulate, release vasoactive amines (principally histamine), lipid mediators (prostaglandins and cysteinyl leukotrienes), cytokines, and chemokines, all of which characterize the immediate phase of the allergic reaction. After the sensitization phase, allergic inflammation and reactions to allergen challenge are observed in the target organ, leading to development of allergic rhinoconjunctivitis, eczema, asthma, or systemic anaphylaxis (Larche, et al., 2006 *Nat Rev Immunol*, 6: 761-771; Romagnani, S. 2004 *J Allergy Clin Immunol*, 113: 395-400).

T$_{h2}$-type cytokines such as interleukin-4 (IL-4), IL-5, IL-9, and IL-13 influence a wide range of events associated with chronic allergic inflammation. IL-4 and IL-13 stimulate the production of IgE and vascular-cell adhesion molecule 1, while IL-5 and IL-9 are involved in the development of eosinophils, and IL-4 and IL-9 promote the development of mast cells. IL-9 and IL-13 help promote airway hyperresponsiveness, while IL-4, IL-9, and IL-13 also promote the overproduction of mucus (Kay, A B 2001 *N Engl J Med*, 344: 109-113; Kay, A B 2001 *N Engl J Med*, 344: 30-37). Regulatory T cells (T$_{Reg}$ cells) have been discovered as another pivotal subset of CD4$^+$ T cells with implications for allergic diseases. Studies in mice model strongly implicate T$_{Reg}$ cells in the suppression of allergic responses, and there is emerging evidence that T$_{Reg}$ cells also control T$_{h2}$-cell responses in humans through the inhibitory cytokines IL-10 and transforming growth factor-β (TGF-β), with atopy resulting from an imbalance between T$_{h2}$ cells and TReg cells (Bacchetta, et al., 2007 *J Allergy Clin Immunol*, 120: 227-235; quiz 236-227; Larche, M. 2007 *Chest*, 132: 1007-1014. T regulatory cells may contribute to the suppression of allergic diseases by suppression of IgE and induction of IgG$_4$, whereas IgA production is enhanced by B-cell activation via TLR7 and TLR9 (Meiler, F 2008 *Allergy*, 63: 1455-1463). The imbalance between T$_{h1}$ cells (IFN-γ producing) and T$_{h2}$ cells play an important role in allergy therapy. Specific immunotherapy is associated with down-regulation of the cytokines produced by T$_{h2}$ cells, up-regulation of cytokines produced by T$_{h1}$ cells, and the induction of regulatory T cells. These changes in turn lead to the inhibition of allergic inflammation, increases in cytokines that control the production of IgE (interferon and interleukin-12), the production of "blocking" antibodies (IgG), and the release of cytokines involved in allergen-specific hyporesponsiveness (IL-10 and TGF-β) (Kay, A B 2001 *N Engl J Med*, 344: 109-113). Another newly identified type of CD4$^+$ T cell has been named the T$_{h17}$ cell, which are associated with neutrophilic inflammation (Stockinger, B 2007 *Immunol Cell Biol*, 85: 83-84). IL-17A is overexpressed in asthmatic airways in association with neutrophil influx and it induces production of the neutrophil chemoattractant IL-8 (CXCL8) by human airway smooth muscle cells (Holgate, S T and Polosa, R 2008 *Nat Rev Immunol*, 8: 218-230). Healthy and allergic individuals exhibit all 3-T$_{h1}$, T$_{h2}$, and T$_{reg}$ allergen-specific subsets-in different proportions (Akdis, M et al., 2004 *J Exp Med*, 199: 1567-1575). Accordingly, a change in the dominant subset and the balance between T$_{h1}$, T$_{h2}$ and T$_{reg}$ cells may lead to either allergy development or recovery.

Microarrays and slabs can be constructed using methods known in the art, including those described in PCT/US2006/036282 (published as WO/2007/035633) and U.S. Ser. No. 61/057,371. The contents of both of these applications are incorporated herein by reference in their entirety. As used herein, "moldable slab" refers to an apparatus which can flex, move or distort, at least in one dimension, when placed in contact with a substrate. For example, in certain configurations the moldable slab may include a material, e.g., an elastomeric material, such that as the moldable slab is placed in contact with a substrate, a substantially fluid tight seal may be formed between the moldable slab and the substrate to retard or to prevent any fluid in the moldable slab from escaping or leaking.

The methods, apparatus and kits described herein may use a moldable array of microwells or chambers (e.g., less than 100 microns in diameter, or 50-100 microns in diameter) to retain one or a few cells in each microwell. The array is placed in physical contact with a substrate in such a manner that the microwells become closed containers or a test apparatus. Incubation of this system allows the cells to produce products, such as antibodies, cytokines and other secreted products, that are then immobilized on the substrate in the regions contacted by the microwells. In this manner, a microarray of the cellular products from each microwell is produced. After incubation of the system for a suitable time, e.g., 1, 5, 30, 40, or 50 minutes to a few hours (1, 3, 6, 12, e.g., 24 hours or less), the microwell array is removed from the substrate, and the immobilized cellular products on the substrate, the microarray or microengraving, may be screened with a known species to determine whether or not the immobilized cellular product(s) associate with the known species.

The soft lithographic technique is used to microengrave a dense array of microwells (0.1-1 mL each) containing individual cells to print a corresponding array of the molecules secreted by each cell. The cells remain in culture in a microwell after the engraving, and the microarrays are interrogated in a manner similar to commercial microarrays of proteins or antibodies—for example, by use of fluorescently labeled reagents and laser-based fluorescence scanners. This method, therefore, enables rapid identification of those cells that exhibit desired properties, such as secretion of an antigen-specific antibody, and their subsequent recovery from individual wells for clonal expansion.

In general, any method that specifically detects a desired cytokine can be used in the methods and compositions of the inventions. Generally, arrays of antibodies (polyclonal or monoclonal) with known specificities are used to detect the presence of a cytokine.

In some embodiments, the cytokine profile tested is a $TH_1$ or $Th_2$ profile. For example, for a detection agent that detects a Th set, the cytokine can be, e.g., IL-17, IL-10, IL-4 and/or IFN-γ. A $Th_2$ set includes, e.g., IL-4, IL-5, IL-13 and/or IL-9. A third profile assesses levels of IgE, $IgG_1$, $IgG_4$ and/or IgGA antibodies. Other cytokines that can be tested include, e.g., IFN-gamma, TNF-alpha, IL-10, TGF-beta, GM-CSF (which mediates differentiation of Th1 and Th2 cells), and IL-17A. Cytokines that are not necessarily from T cells, but which can also be screened include, e.g., IL-2, IL-12, IL-18, IL-8, IL-15, IL-25 (IL-17E), IL-33, TGF-alpha, IL-35, IL-1beta, IL-6, IL-23, IL-22, IL-19, IL-17F, thymic stromal lymphopoietin (TSLP), glycosylation-inhibiting factor (GIF), MARC (Mast Cell Activation-related Chemokine) LTC4, and PGD2. Other chemokines that are tested include CC chemokines (e.g., monocyte chemoattractant protein-1 (MCP-1 or CCL2) and RANTES (CCL5)), CXC chemokines (e.g., IL-8), C chemokines (e.g., XCL1 (lymphotactin-α) and XCL2 (lymphotactin-B)), and $CX_3C$ chemokines (e.g., fractalkine (or $CX_3CL1$).

In general, any known or suspected allergen can be tested. Common food and drug allergies include, e.g., milk, egg, legume (including peanut), tree nut (walnut, cashew, etc.), fish, shellfish, soy, wheat dairy products, egg products, seafood and shellfish. Drug allergens include, e.g., amoxicillin, penicillin sulfa drugs, barbiturates, anticonvulsants, insulin, and iodine. Other common allergens include, e.g., dust, pollen, pet dander, latex, chlorine, insect bites (wasp, fire ant and bee stings).

Single-cell analysis using the methods described herein provides unique advantages to understand the biological process and the mechanism of disease. Microscopic imaging and chemical separations have elucidated unique biological phenomena in single cells that are not discoverable by bulk sampling procedures (Sims, C E and Allbritton, N L 2007 *Lab Chip*, 7: 423-440). One example is the unique patterns of repetitive increase and decrease in $Ca^{2+}$ concentration over time after stimulating single cells (Woods, et al., 1986 *Nature*, 319: 600-602). This phenomenon is hidden when studying a whole population of cells, due to differences in timing and response of individual cells. Single-cell measurements are also valuable for studying populations of mixed cells.

In studies of disease states, analysis of a sample taken directly from a model organism or patient is complicated by the mixture of normal cells with diseased cells. Single-cell studies of tumor biopsies have shown that the majority of cells within a tumor may be normal. Among the abnormal cells; however, significant heterogeneity exists (Fink, et al., 2006 *Exp Toxicol Pathol*, 57: Suppl 2, 25-29; Bodey, B 2002 *Expert Opin Biol Ther*, 2: 371-393). Thus, determination of the molecular characteristics of most tumors is extremely limited by analysis of pooled cell lysates.

Single-Cell Detection

Over the past few decades, series of techniques have been developed for high-throughput studies of the molecular machinery of individual cells. ELISPot (enzyme-linked immunospot) is a common method for detecting cytokine-producing cells at the single-cell level (Czerkinsky, et al., 1983 *J Immunol Methods*, 65: 109-121). In this technology, cells are loaded and grow on a membrane that is functionalized with specific antibodies. During culturing, cytokines produced by each cell are captured by the antibodies around the cells. After detection by another antibody, the secreted product from individual cells is visualized. This method provides both qualitative results of secreted protein and semi-quantitative results of the frequency of responding cells. The disadvantage of this technique is that only one or two kinds of secreting protein can be detected each time and it doesn't assess multiple patterns of secretion from each cell. Also, specific cells are lost after the experiments.

FACS (fluorescence-activated cell sorting) is a type of flow cytometry. Each cell is stained with fluorescently labeled antibodies against either cell surface markers or intracellular proteins. With the development of new detection techniques, up to 19 parameters (17 fluorescent colors and 2 physical parameters) can be detected simultaneously from each cell (Perfetto, et al., 2004 *Nat Rev Immunol*, 4: 648-655), though routine use is typically limited to 6 to 8 colors. FACS is the most common technology used in immunology to study populations of cells. It can analyze several thousands of cells per second. However, it is hard to collect and culture single cells after detection, which makes the kinetic study following one cell impossible. The typical sensitivity of FACS is ~0.1% and requires sufficient staining of the target cells.

Another set of high-throughput techniques aim to detect rare circulating tumor cells (CTC) from blood, such as CTC-chip (Nagrath, et al., 2007 *Nature*, 450: 1235-1239), a microfilter device (Zheng, et al., 2007 *J Chromatogr A* 1162, 154-161), or micropores (Talasaz, et al., 2006 *Conf Proc IEEE Eng Med Biol Soc*, 1: 1838-1841). Some are techniques that improve the efficiency of the detection system, such as rare event imaging system (REIS) (Kraeft, et al., 2004 *Clin Cancer Res*, 10: 3020-3028) and fiber-optic array scanning technology (FAST) (Krivacic, et al., 2004 *Proc Natl Acad Sci USA*, 101: 10501-10504). The advantage of these methods is the ability to screen and isolate rare cells quickly. However, the cell type captured and further analysis is limited.

Lab-on-a-chip (LOC) is another format for single-cell detection. Many systems are based on micro fabrication of channels and microenvironments. Different types of LOC include flow cytometry, electrophoretic analysis of cell contents, microscopic analyses with indicators, cells as small volume reactors, interplay of cells with the microenvironment, and single-cell PCR (Sims, C E and Allbritton, N L 2007 *Lab Chip*, 7: 423-440).

Microengraving for Single-Cell Study and its Advantages

Microengraving is a recently developed technique for rapid, high-throughput, multiplexed screening of individual cells. This technique has been used to screen hybridomas to produce monoclonal antibodies (Love, et al., 2006 *Nat Biotechnol*, 24: 703-707). It was also adapted for the multiplexed interrogation of populations of individual human peripheral blood mononuclear cells from Type 1 diabetic patients for secreted cytokines (IFN-gamma and IL-6), antigen-specific antibodies, and lineage-specific surface markers (Bradshaw, et al., 2008 *Clin Immunol*, 129: 10-18).

In this technology, an array of microwells is molded into a flexible PDMS polymer stamp to isolate individual cells (FIG. 1). Subsequently, the array of wells is applied to a glass slide functionalized with capture antibodies against proteins of interest. After a certain time of incubation, the glass slide is separated from microwell stamp and developed using fluorescently labeled detection antibodies. The stamp with cells is either put back into media for culturing or stained for cell surface markers. Cells of interests are retrieved from the wells. In sum, this technique adapts sandwich enzyme-linked immunosorbent assay (ELISA) to measure protein secretion at single-cell level. Besides providing the information normally given by ELISpot and FACS, this technology also has the ability to trace single cells.

Microengraving Used in Immunological Study

The diversity of cells and multi-functionality of cells in the immune system makes the microengraving technology a useful technique to study single cells of the immune system. With microengraving, the following information is measured from peripheral blood mononuclear cells (PBMCs): 1) frequency of each cell type in the whole population; 2) frequency of certain cytokine or antibody-secreting cells in the whole population; 3) cytokine profiles and its dynamic change at single-cell level; 4) viable clone of interests after detection; 5) functional network of different kinds of immune cells in disease.

The above information can be further used in immunological study, clinical diagnosis, monitor disease development, and treatment evaluation.

Improvements of Microengraving

The invention provides for enhanced detection sensitivity. One of the advantages of microengraving compared with ELISA using bulk cell culture is that cells are trapped in a small volume (~0.1 nl/cell), which results a high local concentration of target proteins. The methods described herein are approximately 10 times more sensitive than surface-based capture of secreted cytokines (e.g., Millipore). On the other hand, directly labeling of fluorescence to detection antibody shows lower sensitivity compared with ELISA, where the signal is amplified by an enzymatic catalytic reaction. The detection sensitivity is about 10~100 times lower than ELISA using the same antibody pairs. The increased local concentration of secreting protein and the decreased signal amplification in microengraving makes the total detection sensitivity not dramatically higher than ELISA.

The invention will be further illustrated in the following non-limiting examples.

Example 1

Optimization of the Process for Cytokine Detection

The protocol for detecting secreted cytokines from array of microwells fabricated by soft lithography was optimized. Different slides, blocking buffers, and capture antibody concentration were tested.

Poly-lysine and epoxides are two commonly used surfaces for slides in protein microarray. Milk and BSA are two common blocking buffers used in western blot and microarray. A gradient of IL-4 capture antibody was spotted on the surface of glass slides (either poly-L or epoxy surface), 2 μl/spot. After incubation at room temperature for 2 hours, the slides were blocked with either 1% BSA or 3% non fat dry milk in PBS for 30 min. Standard IL-4 (500 pg/ml) was added to each spot and incubated for 1 hour at 37° C. Subsequently, 1 μg/ml IL-4 detection antibody conjugated with Dylight 647 was applied as detection reagent. For the control (background), no IL-4 standard was added. A gradient of capture antibody was tested using four parameters in different combinations. Poly-L slides, blocked with milk, and coated with 1025 μg/ml capture antibody provided the best results and additionally provided much better results than the original protocol (epoxy slide, BSA blocking, and 200 μg/ml capture antibody). The optimal mixture was used in the following experiments.

Expanding microengraving into four color detection, based on the four lasers in the GenePix scanner, was tested. Four T cell cytokines IFN-γ, IL-4, IL-10, and IL-17 were chosen. The detection antibodies were labeled with four fluorescent labels separately: IL-17-Dylight 488 (blue), IFN-γ-Dylight 549 (green), IL-10-Alexa Fluor 594 (yellow), and IL-4-Dylight 649 (red). Individual cytokine standards were performed using individual antibody pairs and cytokine standard to test the performance of each antibody pair. The standard curves show the sensitivity of these four cytokine is 200 pg/ml. The multiplexed strategy is to coat the glass with the mixture of all the four capture antibodies and detect with a mixture of detection antibodies. To study the possible cross reaction between different antibodies and cytokines, standard curves were constructed for each single cytokine using a mixture of capture antibodies and detection antibodies. The results show that at higher concentration, some cytokine signals might influence each other. IL-10 has a strong signal at IFN-γ channel when its concentration is above 16 ng/ml; IL-4 and IFN-γ has some signal in IL-10 channel. Based on this data, these four colors can be clearly distinguished if the cytokine concentration is in the range of 1-10 ng/ml.

Multiple Cytokine Detection from Single Cells

In order to test whether the above method has the sensitivity to detect multiple cytokines secreted from cells, PBMCs were stimulated by PHA for 24 hours and loaded onto microwells. The image of some spots were observed after two hours' printing. Single color spots are found on the slide, which shows these four colors are well distinguished among each other. Also, there are some double positive or multiple positive spots, which demonstrate that the functional profile of each cell is different.

Figure 2:
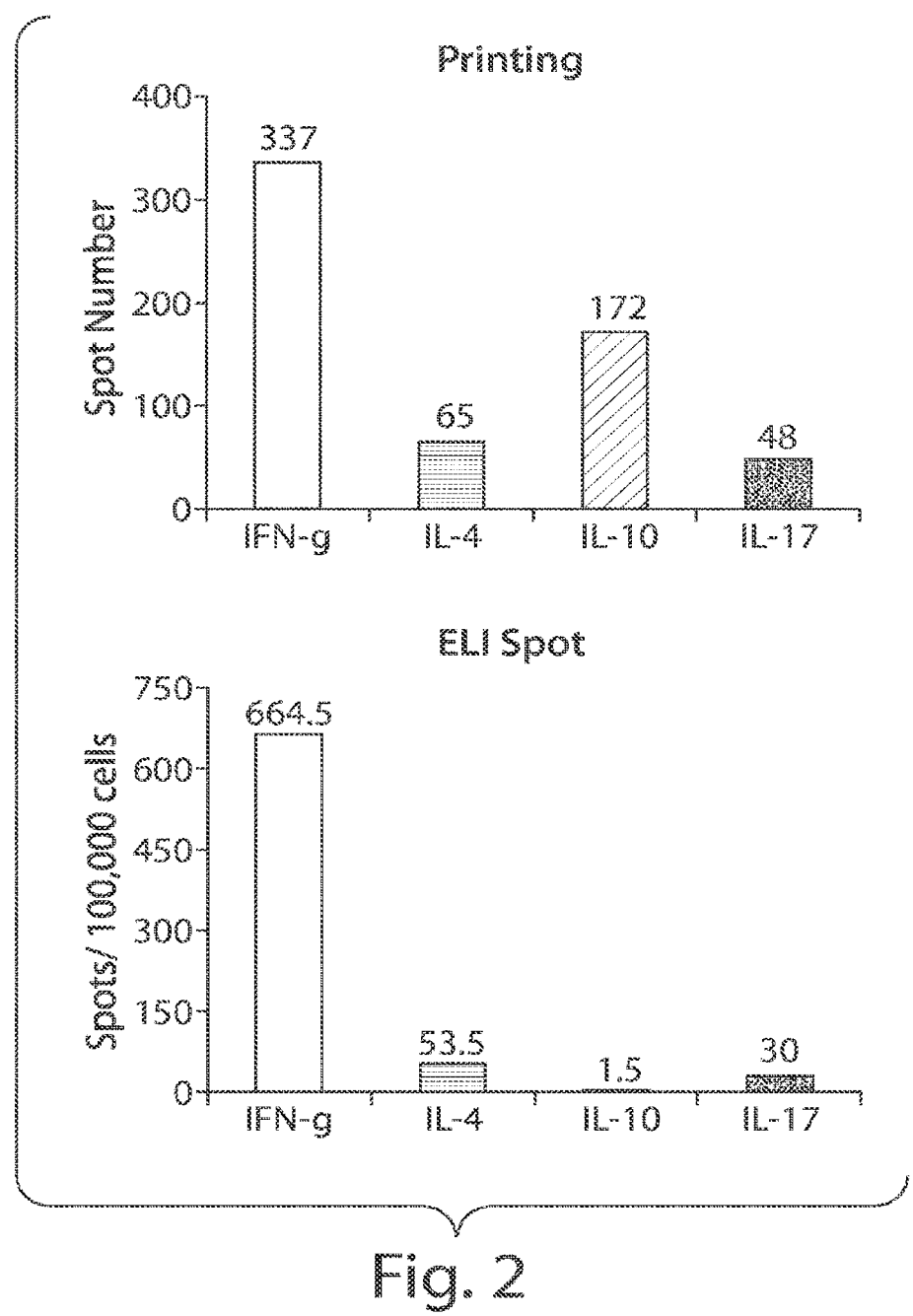
FIG. 2 is a series of bar graphs demonstrating the frequency of cytokine secreting cell measured by microengraving and ELISpot.

In order to compare microengraving and ELISpot, the same set of cells and the same clones of antibodies were used to detect the frequencies of cytokine secreting cells in both methods (FIG. 2). The total number of wells in one stamp was about 80,000, and the loading efficiency was normally 50%. Based on this calculation, the frequency of IFN-γ is the same magnitude in these two methods. Comparing the other three cytokine to IFN-γ, the relative frequency of IL-4 and IL-17 is the same order and microengraving shows a higher sensitivity than ELISpot.

IL-10 frequency is not consistent in these two methods. A possible explanation is that IL-10 antibody used in microengraving is not suitable for ELISpot. However, ELISpot can only detect one parameter from each cell, and it cannot give the information about the frequency of double positive cells. A direct comparison between ELISpot and microengraving is shown in Table 1.

TABLE 1

Comparison of microengraving and ELISpot

| | Microengraving | ELISpot |
|---|---|---|
| Cell | ~$10^5$ | ~$10^5$/well |
| | | *N cytokine |
| Sampling window | 2 h | 24 h |
| Total time | ~7 h | At least 48 h |
| Quantitative determination of rates of secretion | Yes | Limited |
| Retrieve cell | Yes | No |
| Information | more | Less |

Cells Retrieved from Microengraving Maintain their Phenotypes

To determine whether primary cells are still alive after printing, and whether the functional profiles detected by the microengraving are reproducible, CD4$^+$ T cells were loaded in the microwells, and the secretion of IFN-$\gamma$ and IL-17 were measured. Three types of signals were detected: IFN-$\gamma$ positive, IL-17 positive, and IFN-$\gamma$/IL17 double positive. During printing, most of the wells contained 1~2 cells, and some of them contained three cells. After printing, cells in the microwells were cultured for another two days, most of the cells divided, and some of the representative cells are picked out from wells and cultured in 96 wells. After allowing for cell growth, intracellular staining was performed and FACS was used to detect the phenotype.

CD4$^+$ T cells were loaded in the microwells for detecting IL-17 and IFN-$\gamma$. The cells with signal were picked from wells and cultured into clones. Some of the cells retained the same phenotypes as detected in the microengraving. A double negative population was observed. These cells may have lost their cytokine secreting ability during culturing, or there may have been one such cell in the original wells where 2 or 3 cells were loaded. These results demonstrate: 1) through process optimization, the detection sensitivity for single cytokine is at least 200 pg/ml using directly fluorescent labeling; 2) four cytokines are detected simultaneously in microengraving; 3) frequencies of cytokine secreting cells are estimated using microengraving and provide more detailed information compared with ELISpot; 4) cells were viable after two hours of printing and were retrieved from the wells. Some of the cells still keep the original phenotypes.

Example 2

Multiplexed Cytokine Capture

Custom Injection Molds for Production of Arrays of Microwells.

As described above, the methods of the invention include an injection molding process for producing thin (1 mm) arrays of nanowells molded in poly(dimethylsiloxane) that are attached to a standard glass slide. This standardized manufacturing process has provided improved reproducibility of the assays and data collection.

Antibody Validation for Cytokine Detection.

Validation of appropriate pairs of antibodies to detect cytokines of interest is described below. The simple cell-free assay described below mimics the microengraving process that is used to test candidate pairs of antibodies. This flexible assay has allowed for the identification of four distinct panels for detecting sets of cytokines that indicate the skewedness of the Th response and specific Th2 and Th1 responses (IL-4/IL-10/IL-17/IFN$\gamma$; IL-4/IL-5/IL-9; IFN$\gamma$/MIP-1$\beta$/TNF$\alpha$/perforin; IFN$\gamma$/IL-10/IL-17/IL-22). Detection antibodies for two panels of antibodies (IgG1/IgA/IgE/IgG4; IgG1/IgA/IgG3/IgM) have been validated.

Quadriplexed Cytokine Detection from Single Cells.

Figure 3:
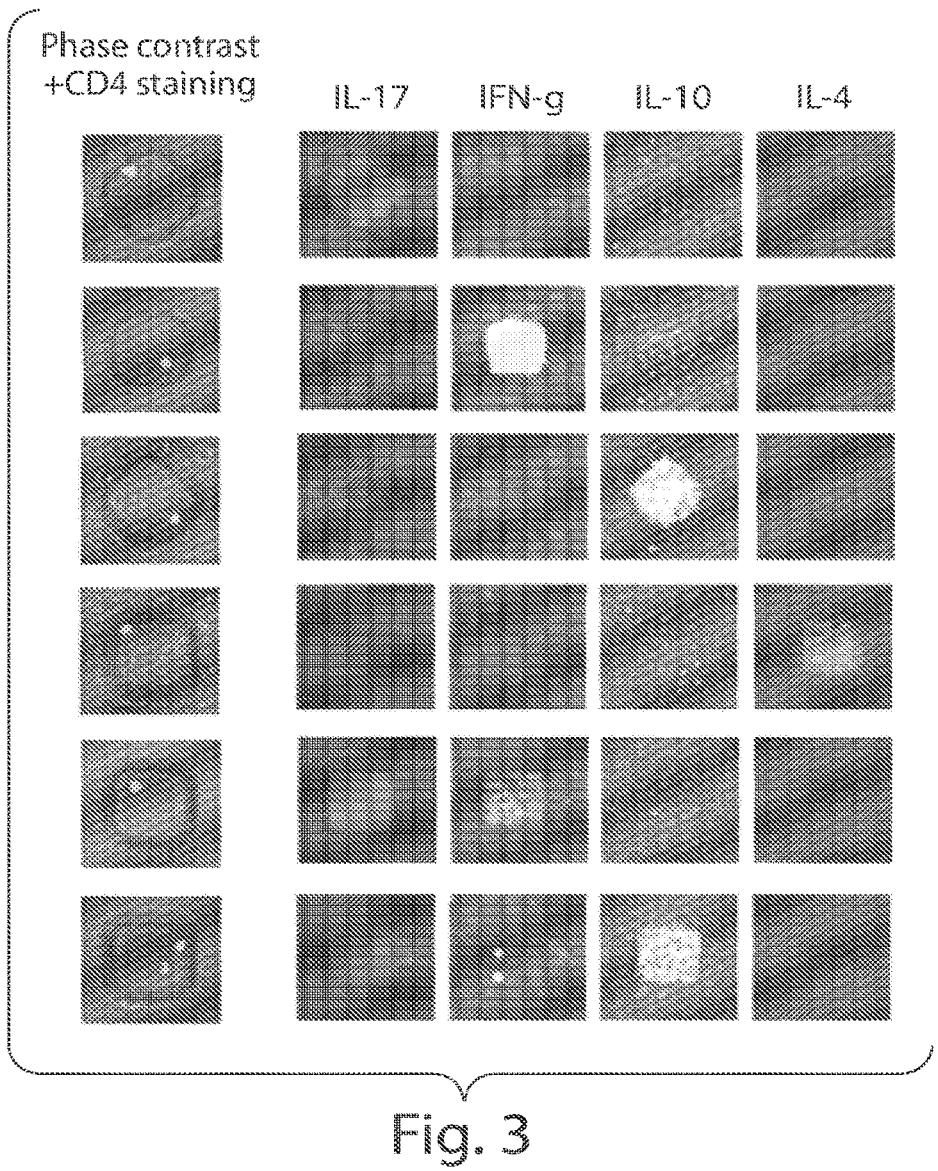
FIG. 3 is a series of photomicrographs illustrating quadriplexed cytokine profiles for CD4+ T cells generated by microengraving.

Described below is quadriplexed detection of two sets of cytokines from single cells. FIG. 3 presents the results of an assay that indicates the skewedness of the T cell response (IFN$\gamma$/IL-4/IL-10/IL-17). In this experiment, PBMCs were stimulated with anti-CD3 and anti-CD28. CD4+ T cells were separated by negative selection, stained with a fluorescent surface marker ($\alpha$CD4-Alexa 647), and loaded onto an array of microwells. The array was placed in contact with a glass slide functionalized with capture antibodies for IL-4, IL-10, IL-17, and IFN$\gamma$. After 2 h incubation, the array was removed and imaged. The slide was stained and imaged on a Genepix microarray scanner. The images were correlated for each well. Each well is 50 $\mu$m×50 $\mu$m×50 $\mu$m. FIG. 4 shows the results of an assay that indicates the breadth of the Th2 response (IL-4/IL-5/IL-13/IL-9). In this experiment, PBMCs were stimulated with anti-CD3 and anti-CD28. CD4+ T cells were separated by negative selection, and loaded onto an array of microwells. The array was placed in contact with a glass slide functionalized with capture antibodies for IL-4, IL-5, IL-13, and IL-9. After 2 h incubation, the array was removed and imaged. The slide was stained and imaged on a Genepix microarray scanner. The images here are correlated for each well. Each well is 50 $\mu$m×50 $\mu$m×50 $\mu$m.

Particularly noteworthy is the detection of IL-4 in these assays—a cytokine that is very difficult to detect by traditional ELISpot. These functional measurements have also been coupled with automated image collection of the cells in the nanowells. In this manner, the lineages of individual cells are matched with their secretion profile. A custom image analysis script has been developed for translating the 1728×N channels of images collected into a list of cells with associated grey-scale values indicating the level of expression of specific surface-expressed markers (e.g., CD4, CD8).

Cytokine Profiles of Mitogen-Stimulated Cells.

Figure 5A:
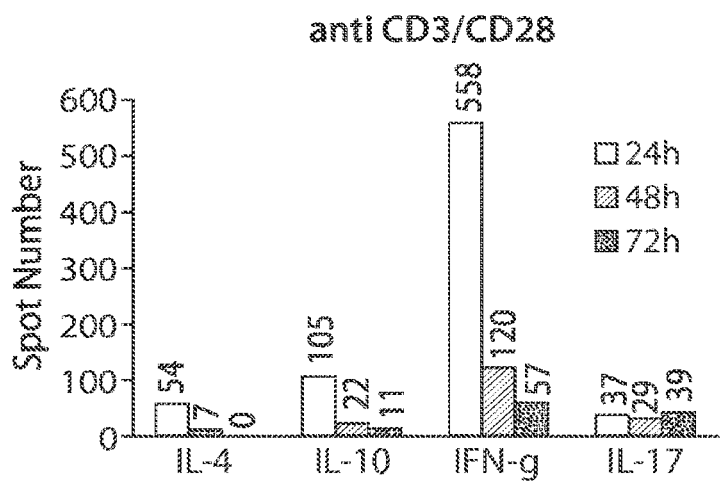
FIG. 5 is a series of bar charts demonstrating quadriplexed cytokine assays for human PBMCs stimulated with (a) anti-CD3/anti-CD28, (b) phytohemagglutinin, and (c) pokeweed mitogen. The data show the number of spots detected by microengraving after 24 h, 48 h, and 72 h of stimulation.
Figure 5B:
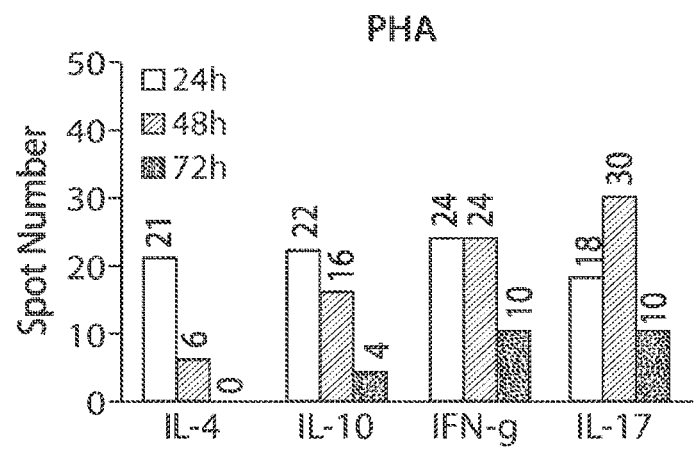
Figure 5C:
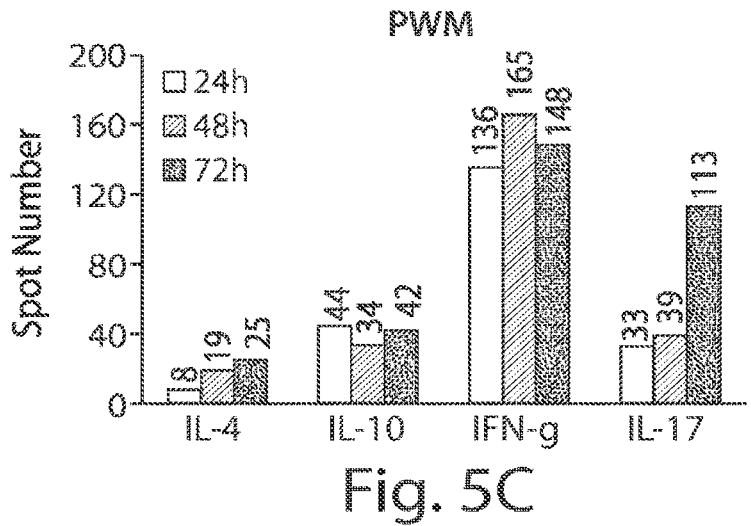

To validate the multiplexed cytokine assay, peripheral blood mononuclear cells (PBMCs) from healthy donors were stimulated with a pair of mitogens known to induce cytokine responses (pokeweed and phytohaemaglutinin, PHA) and a polyclonal stimulus for T cells (anti-CD3/CD8). Following a defined period of stimulation, the number of spots detected on the cytokine microarrays generated by microengraving were assessed (FIG. 5). These data indicated distinct differences among the responses detected as a function of stimulant and time of exposure. Comparisons to conventional ELISpot assays for these activation conditions also corroborated the data.

Example 3

Single-Cell Multidimensional Cytokine Profiles

The cytokines released by lymphocytes are a measure of the cells' functions and influence on the evolution of an immune response. As described below through both numerical simulations and experimental validation, microengraving—a technique for capturing secretions from single cells—provides quantitative measurements of both the frequencies and the distribution in rates of secretion for up to four cytokines released simultaneously from individual viable cells. These multidimensional measures resolve the magnitude and intensities of responses of cells exposed to stimuli with greater detail and sensitivity than single-parameter functional assays. Using this approach, it is shown that the median rate of secretion of IFN$\gamma$ increases in lymphocytes producing two or three cytokines simultaneously, but that other cytokines (IL-2 and TNF$\alpha$) do not exhibit a similar increase. Furthermore, the rates of secretion of IFN$\gamma$ and IL-2 are not correlated in cells producing both cytokines, while IL-2 and TNF$\alpha$ do exhibit a positive correlation.

Distinct functional responses, such as the secretion of one or more cytokines or proliferative capacity, distinguish unique subsets of lymphocytes that may be associated with the quality of an immune response (Pantaleo and Harari, 2006 *Nat Rev Immunol,* 6:417-423). Resolving heterogeneity among subsets of cells requires analytical methods that yield multiple measures of the breadth and quality of functions exhibited by individual lymphocytes (Seder, et al., 2008 *Nat Rev Immunol*, 8:247-258).

Existing analytical methods assess the frequencies, magnitude and number of cytokines produced by individual cells. ELISpot directly measures secretion to determine the frequencies of cytokine-producing cells, but quantifying the subtle differences among cells in a population is difficult. The intensities of spots can indicate the rates of secretion (Henn, et al., 2009 *J Immunol*, 183:3177-3187), but poor sensitivity requires integrating signals over 12-48 h to detect most cytokines (rates <<100 molecule/s). Intracellular staining (ICS) for multiparameter cytometry has become a common alternative to assess the number and magnitude of cytokines expressed by single cells (Kannanganat, et al., 2007 *J Virol*, 81:8468-8476; Darrah, et al., 2007 *Nat Med*, 13:843-850). Mean fluorescence intensities (MFI) provide a relative measure of the quantity of a protein trapped intracellularly, but these values are difficult to compare among independent samples. Furthermore, ICS measures the productive capacity of a cell when prohibited from secretion, and may not accurately reflect the quantity of cytokine that would have been secreted by the cell. Two modified approaches for flow cytometry—'artificial receptors' and microbeads (Manz, et al., 1995 *Proc Natl Acad Sci USA*, 92:1921-1925; Powell and Weaver, 1990 *Biotechnology (N Y)*, 8:333-337)—allow the capture of secreted cytokines near the extracellular surface of the cell. Analytical models for the mass transport in these two processes indicate, however, that the rate of diffusion of released cytokines into the bulk media limits the sensitivity of these measurements for poor secretors and can introduce cross-contamination among cells (Frykman and Srienc, 1998 *Biotechnol Bioeng*, 59:214-226). Encapsulation of cells at cold temperatures in polymeric matrices may also perturb secretion.

The long periods required to accumulate cytokines or to overcome limitations in sensitivities of assays has limited the study of the dynamics of cytokine release by individual primary cells. Described herein is a new single-cell analytical technique that makes it possible to generate integrated, quantitative measurements of the cytokines released from individual viable cells. The microengraving method (Love, et al., 2006 *Nat Biotechnol*, 24:703-707) has been modified to assign rates of secretion for multiple cytokines simultaneously from single cells with sensitivities that exceed current approaches by one to two orders of magnitude. The data enhance the differentiation of functional responses between individuals and reveal the fine dynamics of secretion of cytokines in multifunctional cells.

Modeling and Numerical Simulations

To calculate the concentration of analytes in the microwells, the following assumptions were made: a constant rate of secretion for a given analyte and that the analytes only bind specifically to the functionalized glass surface:

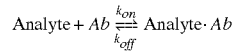

The time-dependent diffusion of analytes inside the microwells was $$\frac{\partial C}{\partial t} - D\nabla^2 C = 0$$

where C is the concentration of analyte in the media, D is the diffusion coefficient of analyte, and t is the incubation time. COMSOL Multiphysics 3.3 (COMSOL AB. Stockholm, Sweden) was used to solve the partial differential equations relating the secretion, diffusion, and binding of analytes with a specific capture Ab. Table 2 lists the system parameters used in the simulations.

TABLE 2

Values of parameters used in simulations

| Parameters | Values |
| --- | --- |
| Well size | 50 μm × 50 μm × 50 μm |
| Cell diameter | 10 μm |
| Diffusion coefficient (D) | $10^{-10}$ m²/s |
| Association rate constant ($k_{on}^s$) | $10^5$-$10^6$/M/s |
| Dissociation rate constant ($k_{off}^s$) | $10^{-3}$-$10^{-4}$/s |
| Rate of secretion (κ) | 1-100/cell/s |
| Density of total binding sites ($\theta_0$) | $10^{-8}$-$10^{-10}$ mol/m² |

PBMCs Isolation

Venous blood was drawn from healthy controls into green-capped, lithium heparin tubes (Kendall) with institutional Internal Review Board Approval. PBMCs were separated using density centrifugation on Ficoll-Paque PLUS (GE Healthcare). PBMCs were suspended at $10^6$/mL in RPMI 1640 medium (Mediatech), supplemented with 10% FBS, 2 mM L-glutamine, 10 mM HEPES, 100 U penicillin, 100 mg/mL streptomycin, 0.1 mM non-essential amino acids, and 1 mM sodium pyruvate.

Preparation of Cell-Loaded Microwells for Microengraving

The experiments were performed as previously described with some modifications as noted (Love, et al., 2006 *Nat Biotechnol*, 24:703-707; Bradshaw, et al., 2008 *Clin Immunol*, 129:10-18). Briefly, an array of microwells was manufactured by injecting a silicone elastomer (polydimethylsiloxane, PDMS; Dow Corning) into a custom-built mold and cured at 80° C. for 1 h. The arrays contained 84,672 microwells (each 50×50×50 μm³) (Ogunniyi, et al., 2009 *Nat Protoc*, 4:767-782). After exposing an array to an oxygen plasma for 30 s (Harrick PDC-32G), a cell suspension (~2×10⁵/mL) was placed on the surface of the array, and the cells were allowed to settle into the wells by gravity at a density of ~1 cell per well. After rinsing excess cells from the surface of the array with media, the loaded device was then placed onto a glass slide coated with capture Abs—specific details for each assay are described below.

IL-6 Detection from PBMCs

Poly-L-lysine slides were prepared according to published protocols and used to immobilize capture Abs. Anti-human IL-6 (40 μg/mL, MAB206, R&D) and anti-human IgG (10 μg/mL, 81-7100, Invitrogen) were diluted in borate buffer (Ogunniyi, et al., 2009 *Nat Protoc*, 4:767-782), applied to slides for 1 h at 25° C., rinsed with PBS, and dried. To stimulate IL-6 secretion, LPS (10 μg/mL), PHA (5 μg/mL), and PWM (5 μg/mL) were added individually to PBMCs in round bottom 96-well plates and incubated at 37° C. with 5% $CO_2$ for desired time. Prior to loading the arrays of microwells, the PBMCs were stained with Calcein violet AM (Invitrogen). The cell-loaded arrays were then imaged on an automated inverted epifluorescence microscope (Zeiss) equipped for live-cell imaging (temperature and $CO_2$ control). The arrays were mounted face-up on the microscope with a coverslip (with media containing specific stimuli). The array of wells was then rinsed gently with media containing a trace amount of human serum (1:40,000) (to label the locations of all microwells with human Ig) and immediately applied onto a glass slide bearing capture Abs. The combined array and glass slide was held together under light compression in a hybridization chamber (Agilent Technologies, G2534A) and incubated at 37° C. In the measurements taken over time, half of the cells were collected for mRNA quantification at each time point. After printing, Alexa Fluor 488-labeled anti-human IL-6 (R&D) and Alexa Fluor 700-labeled anti-human IgG (Jackson ImmunoResearch) were used for detection. To label the cells after microengraving, 10 µg/ml of CD3-Alexa Fluor488, CD11b-Alexa Fluor568, and CD14-Alexa Fluor 660 were added to the array of wells. After 30 min at 4° C., the array of wells was washed with PBS and imaged. (All Abs were labeled with Alexa Fluor-NHS esters (Invitrogen) as indicated.)

Real Time PCR

RNA from PBMCs was purified using the absolutely RNA microprep kit (Stratagene). cDNA was made using a Taqman kit with supplied random hexamers (Applied Biosystems). The IL-6 primers and probe were obtained from Applied Biosystems and used according to recommended procedures.

Multiplexed Detection of Cytokines

Pairs of Abs used for multiplex cytokine detection were: IFNγ (MABTECH), IL-17 (eBioscience), IL-2 (R&D), and TNFα (BD). For capture, a mixture of capture Abs (10 µg/ml each) were applied to the glass slides. PBMCs were stimulated by PMA (10 ng/mL) and ionomycin (1 µg/mL) for 6 h, then stained with Calcein violet AM, and imaged in microwells as described above. The array of wells was rinsed with serum-free media and immediately applied onto a glass slide bearing capture Abs. After printing, a mixture of Abs—IL-17 (Alexa Fluor 488), IFNγ (Alexa Fluor 555), IL-2 (Alexa Fluor 594), TNFα (Alexa Fluor 700)—were used for detection. To label the cells after microengraving, 10 µg/mL of CD3 (Alexa Fluor 488), CD8 (Alexa Fluor 568), and CD4 (Alexa Fluor 660) were added on the array of wells. After 30 min at 4° C., the array of wells was washed by PBS and imaged.

Data Analysis

Figure 20:
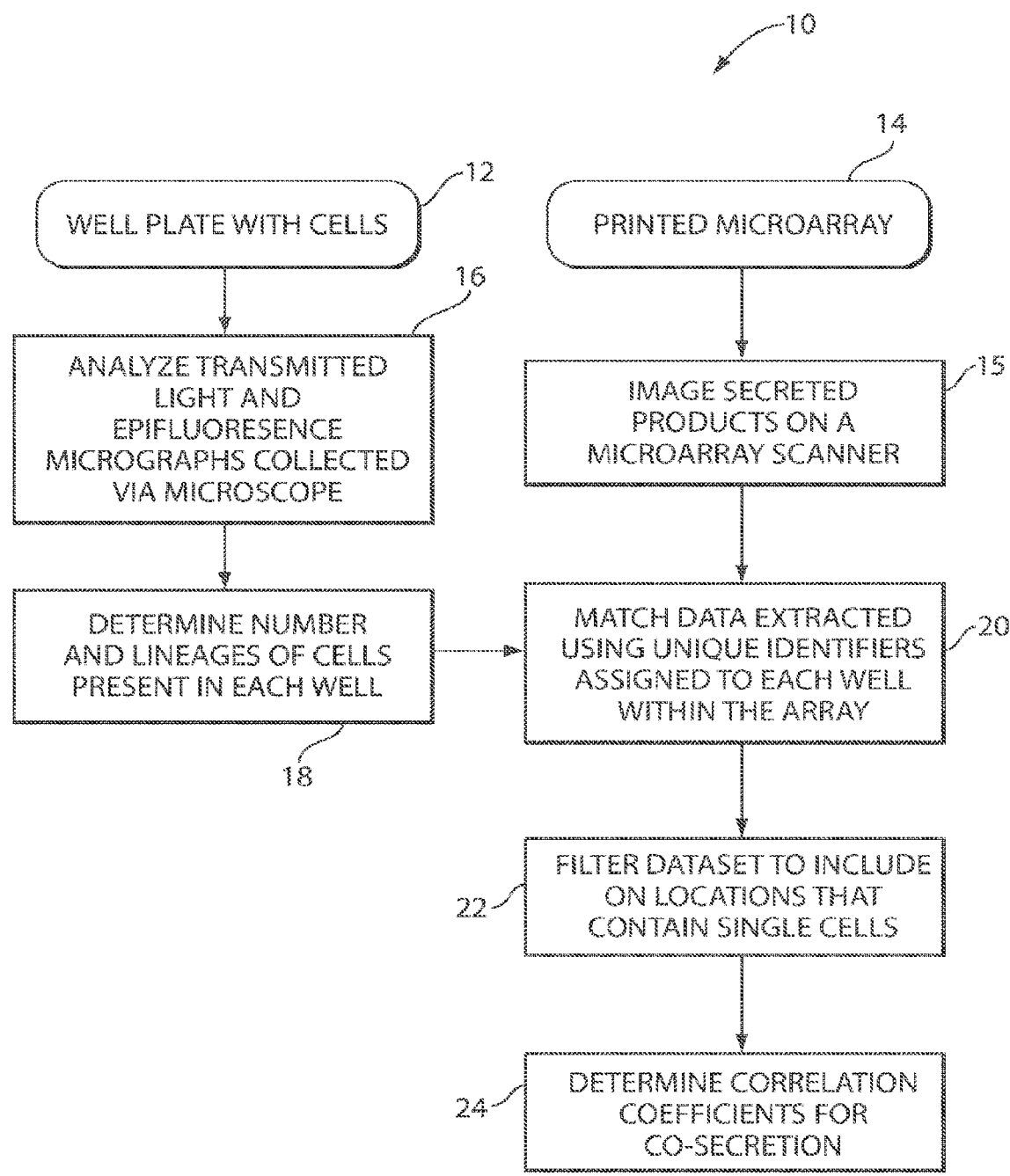
FIG. 20 is a schematic diagram depicting the analysis of microarray data.

In operation, referring to FIG. 20, a process 10 for analyzing secreted products includes the stages shown. The process 10, however, is exemplary only and not limiting. The process 10 may be altered, e.g., by having stages added, removed, or rearranged. The printed microarrays of cytokines 14 can be imaged on a microarray scanner 15 (e.g., GenePix 4200AL, MDS) and analyzed using the accompanying software (e.g., GenePix 6.1). Transmitted light and epifluoresence micrographs collected from a microscope can be analyzed 16 to determine the number and lineages 18 of cells present in each well 12. The data extracted for both the array of cells and the printed microarrays can be matched 20 (e.g., in MS Excel) using unique identifiers assigned to each well within the array. The dataset can be filtered 22 to include the locations in the array 12 that contained only single cells matched to secreted proteins on the corresponding microarray 14 for subsequent analysis (e.g., in Excel or MATLAB (The Mathworks, Natick, Mass.)). The distributions of the rates can be compared using a two-sample Kolmogorov-Smirnov test and correlation coefficients for co-secretion can be calculated using the Spearman rank correlation 24.

Figure 21:
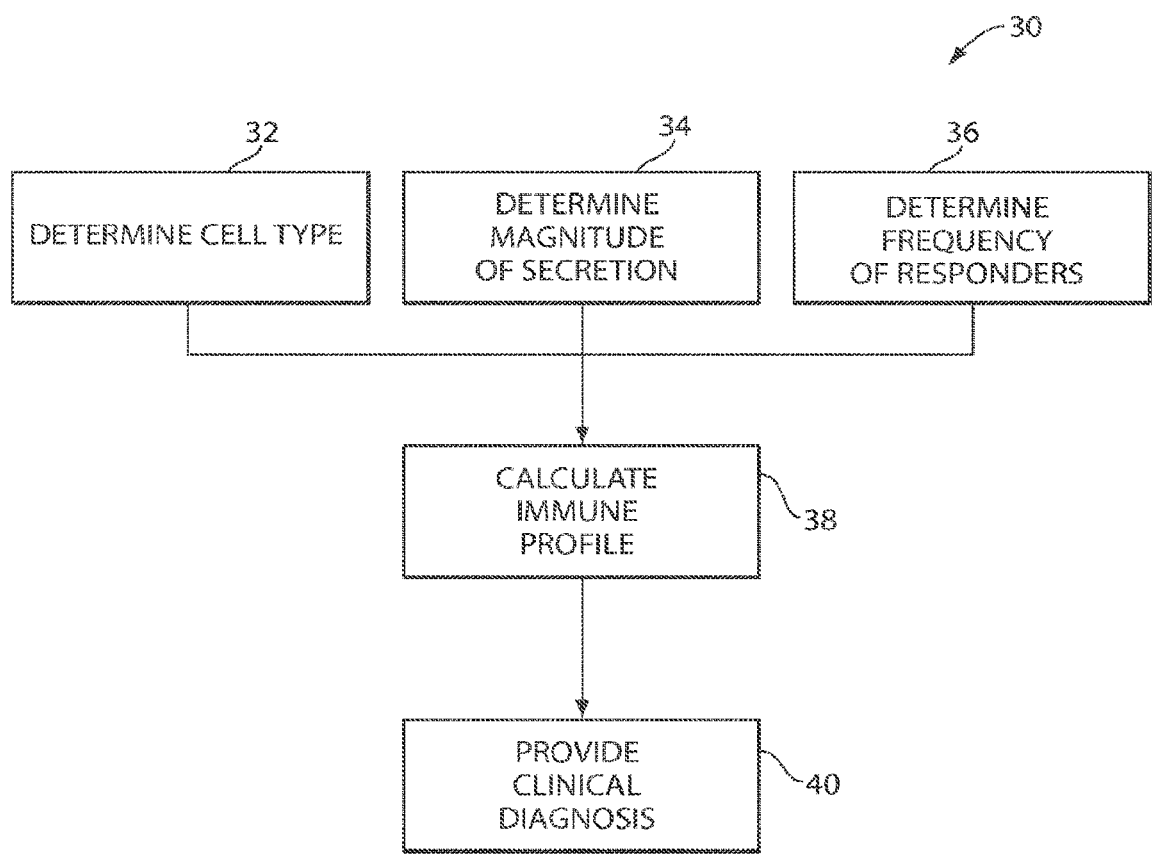
FIG. 21 is a flow chart demonstrating the calculation of immune profile based on cell type, magnitude of secretion, and frequency of responders.

In operation, referring to FIG. 21, a process 30 for creating an immune profile 38 for the purposes of providing a clinical diagnosis 40 is carried out by determining cell type 32, magnitude of secretion 34 and frequency of responders 36, the integration of each dataset yielding an immune profile indicative of a physiological state of the recipient from which the analyzed cell was obtained.

Quantitative Microengraving for Assessing Rates of Cytokine Secretion

Figure 6A:
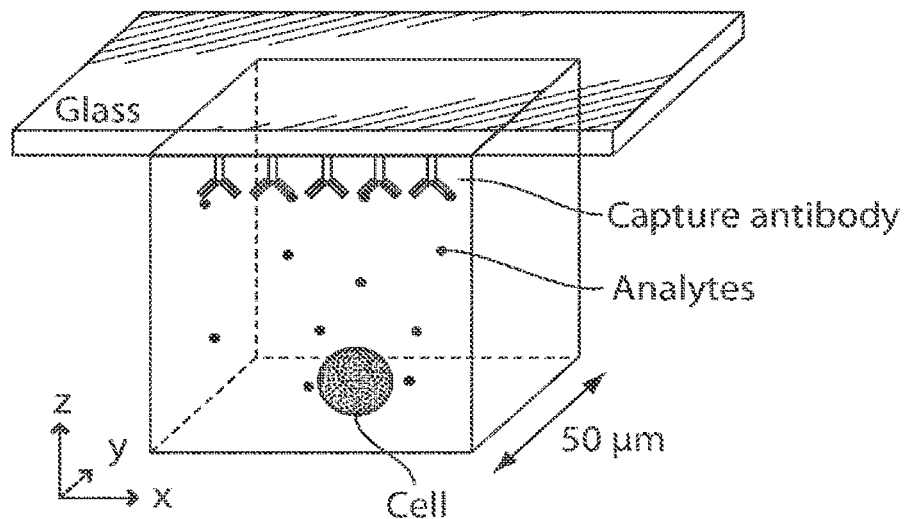
FIG. 6 shows a series of graphs demonstrating the quantification of cytokine secretion from single cells. (A) Schematic of the configuration of one microwell containing a single cell during microengraving. (B) Plot of the calculated amount of analytes accumulated in the media (○) and on the surface of the glass (●) during microengraving when the cell secretes at a constant rate of 10 molecules/s. (C,D) The production of IL-6 by human PBMCs after stimulation with LPS for 3, 6, or 12 h. (C) Histogram of the distribution of rates of secretion of IL-6 measured by microengraving after each stimulation. (D) mRNA level of IL-6 measured by quantitative PCR. (E) Histograms of the distribution of rates of secretion of IL-6 measured by microengraving from two donors after stimulation with LPS, PHA and PWM. The value n indicated in (C) and (E) is the normalized total number of cells under each curve.
Figure 6B:
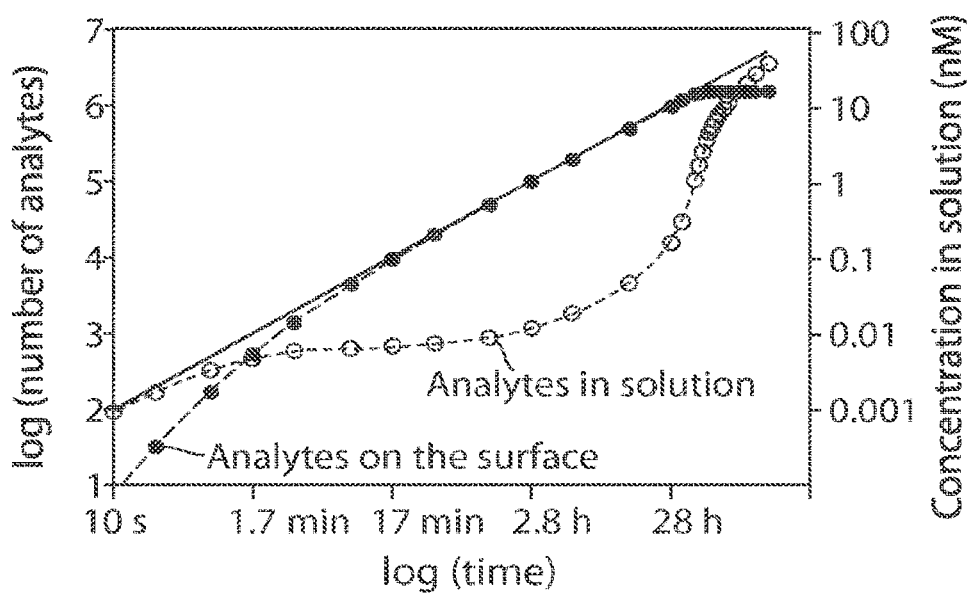

Microengraving uses an array of microfabricated wells to confine viable cells temporarily in subnanoliter volumes with minimal perturbations; one internal surface of the volume supports an Ab to capture protein secreted from the cell (FIG. 6A). After incubation (~1-2 h), the capture surface is removed and then interrogated by applying fluorescent Abs (Bradshaw, et al., 2008 Clin Immunol, 129: 10-18). To determine the optimal conditions under which microengraving would allow quantitative measurements of secretion, a series of differential equations and numerical simulations were used to model the mass transport for a single cell confined to an individual volume. The simulations indicated three regimes describe the temporal relationship between the amount of protein captured on the surface and that in the volume (FIG. 6B). In the intermediate regime (~30 min to >20 h), the amount of protein captured on the surface approximates the total amount of protein secreted by the cell.

Figure 7A:
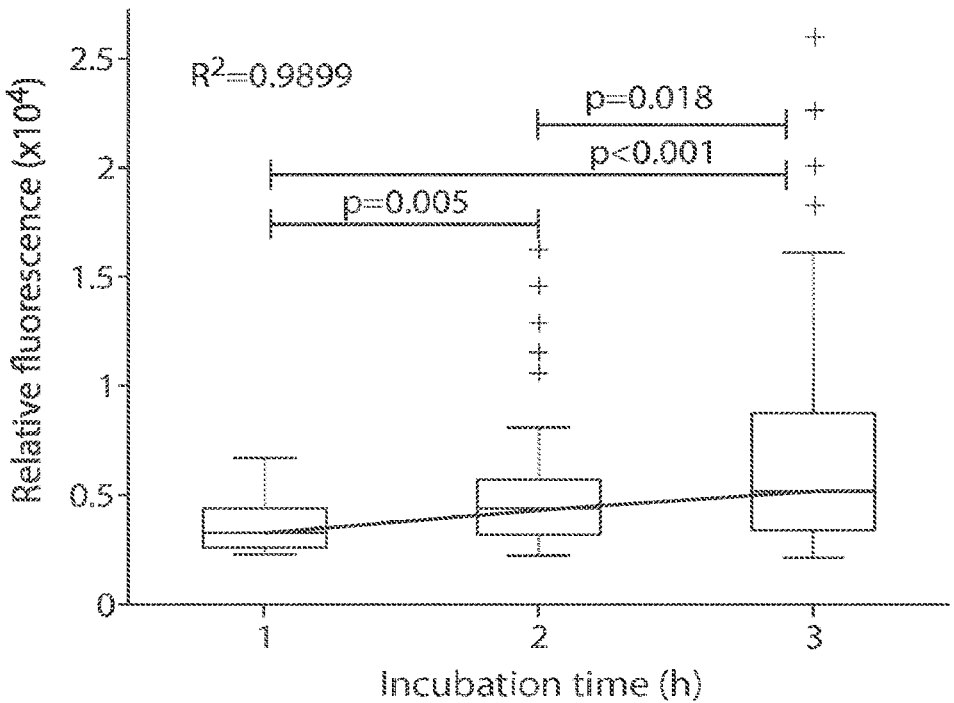
FIG. 7 is a pair of graphs demonstrating experimental analysis of single-analyte measurements using microengraving. (A) Measurement of IL-6 secreted by individual human PBMCs. Cells were stimulated for 48 h with LPS (10 μg/mL) and PWM (5 μg/mL). Boxplot of relative fluorescence intensity of captured IL-6 as a function of incubation time. The minimum number of events included in each box was 35. The solid line was fit by linear regression of the median values. Statistics were determined by two-tailed Student's t-test. (B) Measurement of the secretion of antibodies from mouse hybridoma cells HYB 099-01 (Anti-ovalbumin, Statens Serum Institute). Secreted IgG was captured by a mixture of two goat anti-mouse IgG (from Zymed and Southern Biotech, 50 μg/mL of each) and detected by ovalbumin-Alexa 555 (Invitrogen, 2 μg/mL). Numbers of live cells in microwells were determined by Calcein violet AM (Invitrogen) staining after microengraving. The median values of the signals were plotted as a function of the numbers of cells presented in each well for three different incubation times (15, 30, and 45 min). Solid lines were fit by linear regression.
Figure 7B:
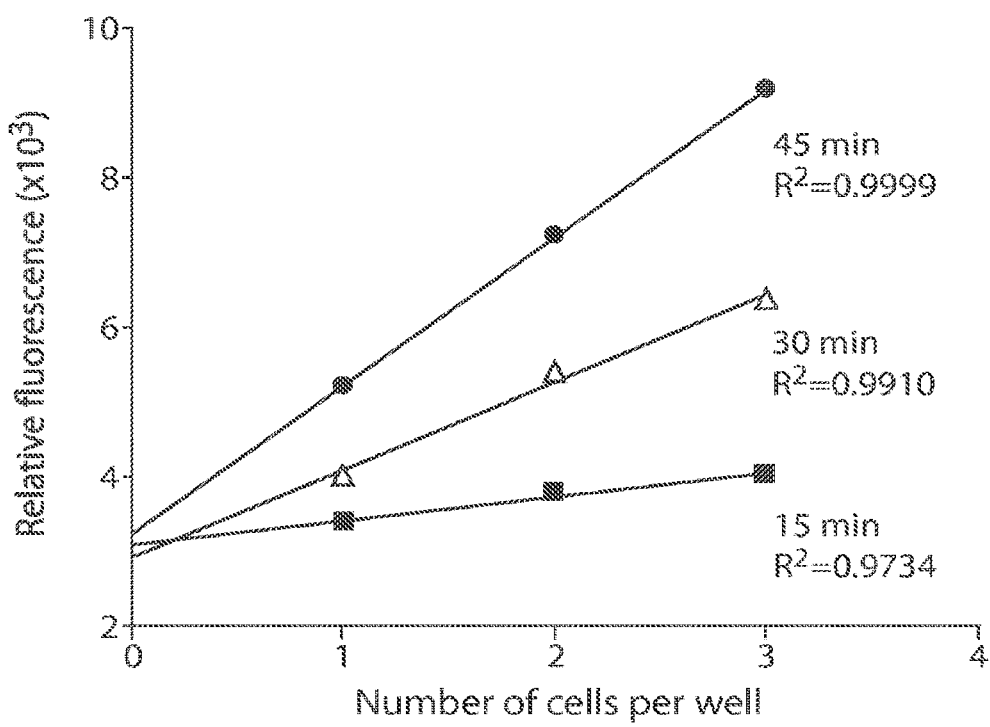
Figure 8:
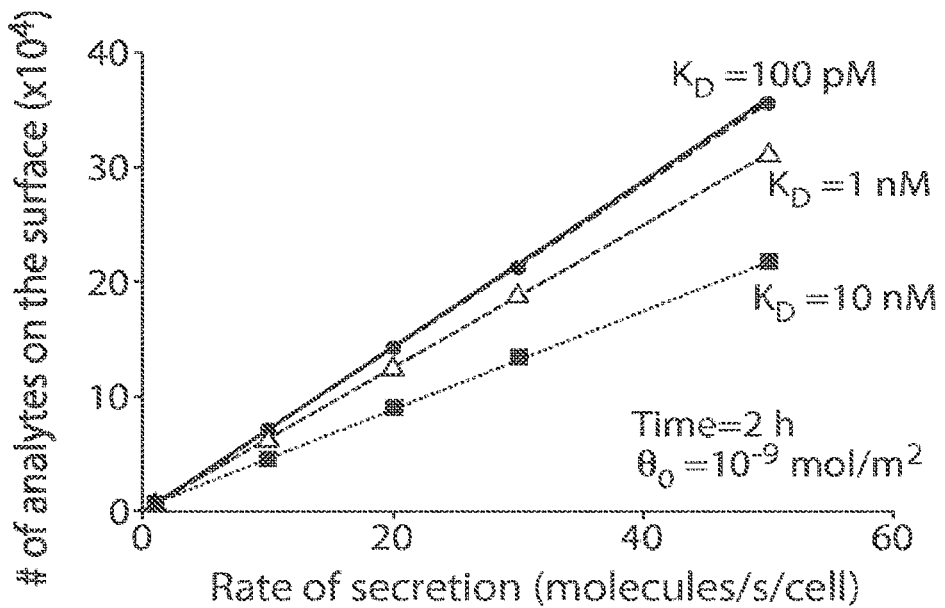
FIG. 8 is a line graph that shows the calculated number of analytes captured as a function of the rate of secretion and affinity for capture antibodies ($K_D$). The solid line represents the total quantity of analytes secreted as a function of time. $\theta_0$ is the estimated density of binding sites on the glass. These calculations suggest that low affinity capture antibodies ($K_D$=10 nM) may underestimate the rates of secretion by approximately twofold.
Figure 9A:
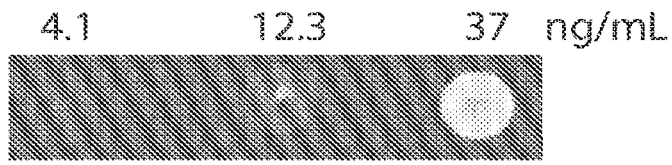
FIG. 9 is a micrograph of a standard reference slide (A) and a sample calibration curve (B) used to calculate the rate of secretion from the cells. A series of diluted, fluorescently labeled detection antibody was spotted on the glass (1 µL/spot) at the concentrations indicated, and the mean fluorescence intensity of each spot was plotted to generate the calibration curve (solid line).
Figure 9B:
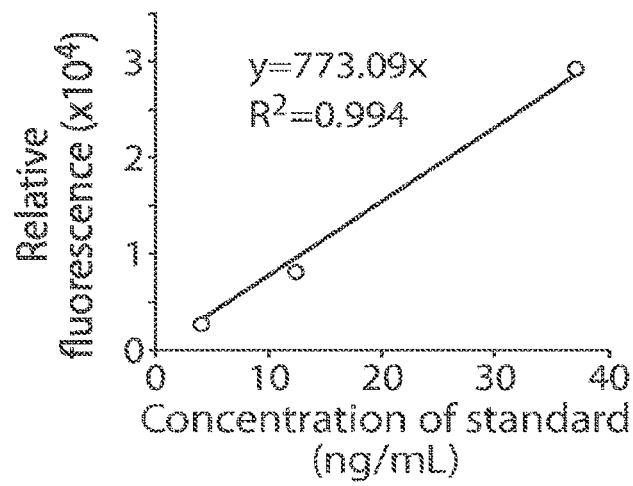

Assuming a constant release of analytes by the cell, the model suggested that the amount of analyte captured should increase linearly with either time or the number of cells per well. Both predictions were experimentally validated using human PBMCs and mouse hybridoma cells (FIG. 7). These results imply that the variations in MFI of captured protein measured for cells at a fixed time-point accurately reflect the variations in the amounts of proteins secreted, and also, therefore, in the average rate of secretion (FIG. 8). To convert MFI into a rate for a given cell, a standard reference comprising known amounts of fluorescent detection Ab was used to translate MFI into a finite quantity of captured analyte; dividing this amount by the time of incubation yields the average rate of secretion from a single cell (FIG. 9). Together, the model and these data demonstrate that microengraving provides an efficient and quantitative assessment of the total quantity of protein secreted over a defined period.

Quantification of Frequency and Magnitude of IL-6 Released from PBMCs

Figure 6C:
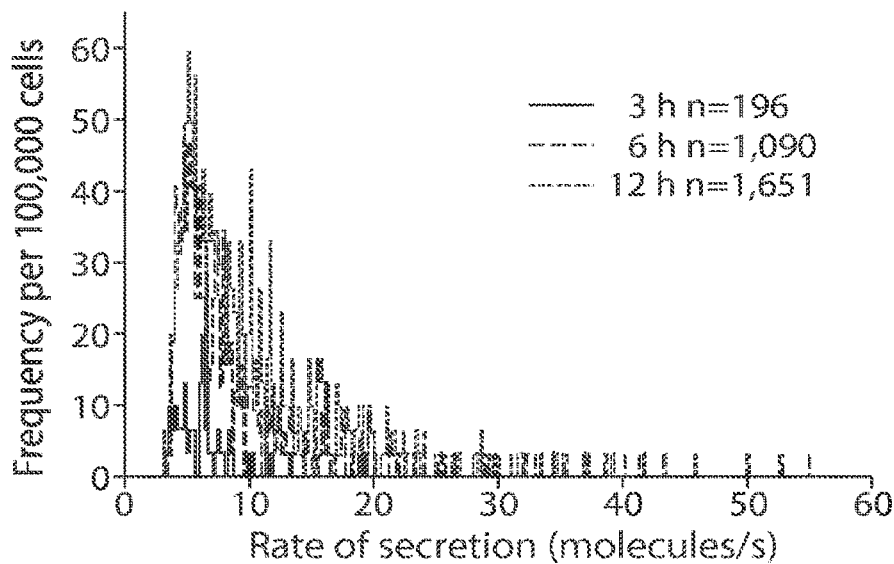
Figure 6D:
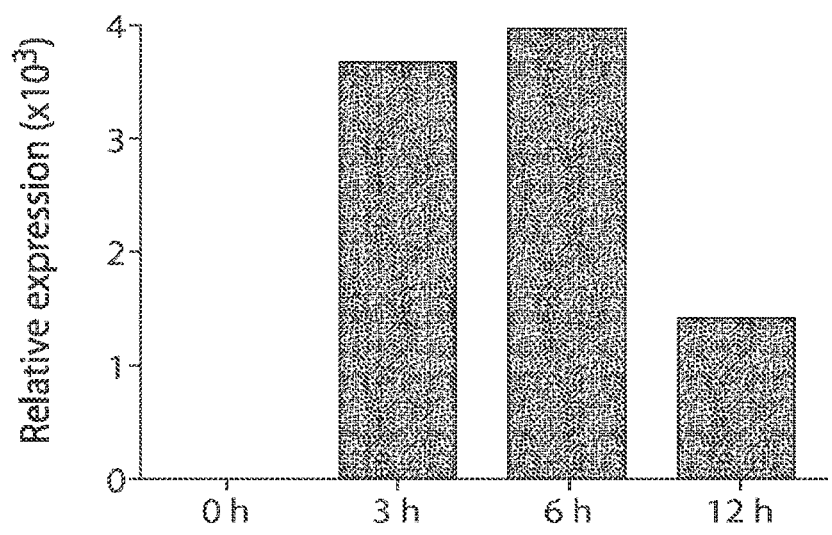

To evaluate the sensitivity of our measurements, both the frequencies and rates of secretion of IL-6 released from human PBMCs after three intervals of stimulation (3, 6, and 12 h) with LPS were measured. The measured responses showed that both the frequency of IL-6-secreting cells and the mean rate of secretion per cell increased monotonically from 3 to 12 h (especially between 3 and 6 h) (FIG. 6C). The expression of mRNA encoding IL-6, however, peaked at 6 h (FIG. 6D); this observation confirms that the timing of transcription may not necessarily correlate with the timing of secretion of a protein. Most of the cells secreting IL-6 were CD11b$^+$ (44.8%) and CD11b$^+$CD14$^+$ (26.9%), while a small population was CD3$^+$ (4.7%). The distribution of rates of secretion among these cells did not differ significantly, suggesting they all have similar secretory capacities.

Figure 6E:
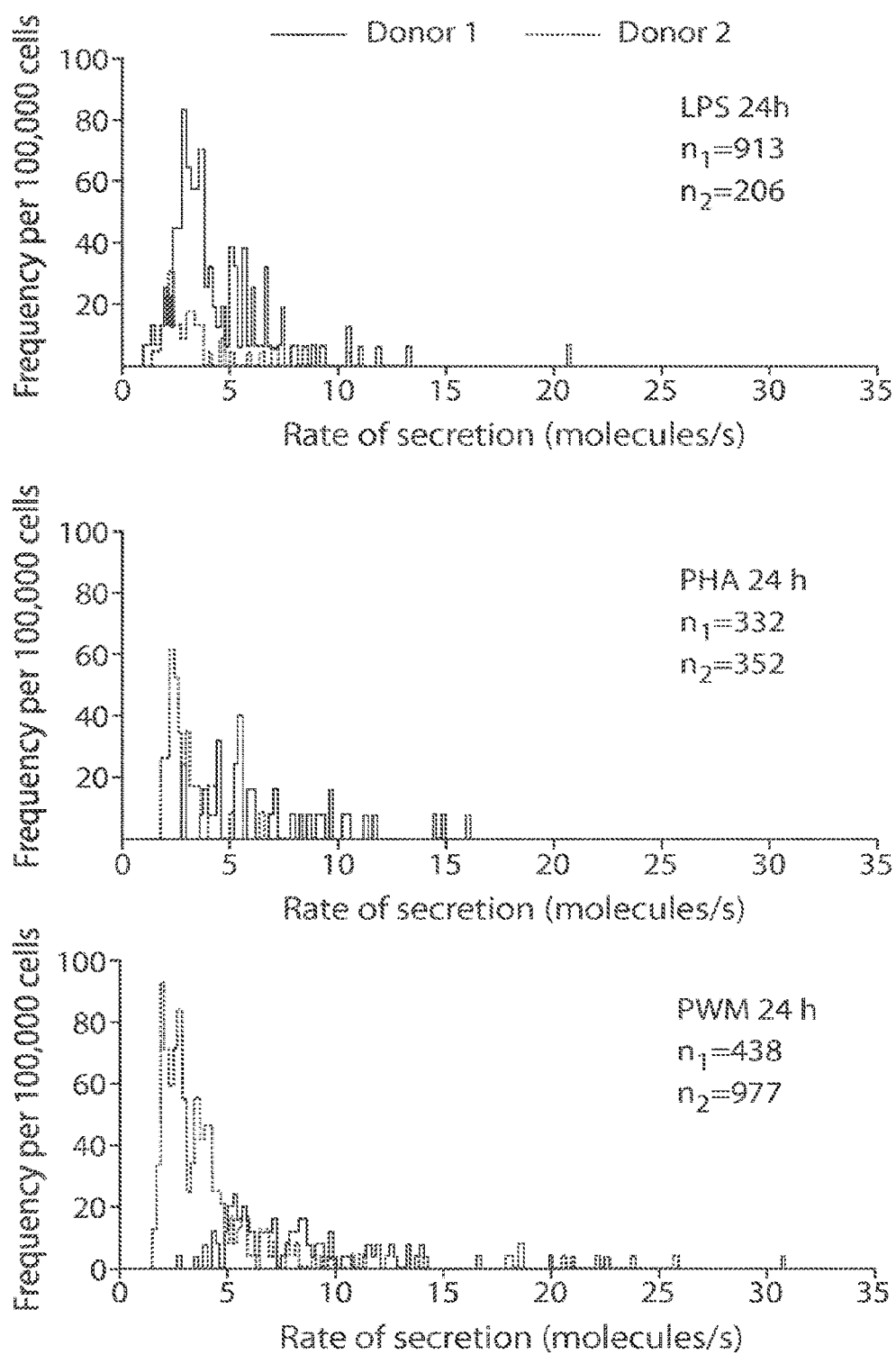

Next, the distributions of rates of IL-6 secretion were examined to distinguish responses between individuals after exposing their PBMCs to different stimuli. The measurements showed that responses of cells from the same donor exhibited strong variations in both the frequency and magnitude (rates) after different stimulations, and that this combination of responses was unique to the individual (FIG. 6E). For example, Donors 1 and 2 exhibited similar frequencies of responding cells after stimulation with PHA, but the distributions in the rates of secretion were quite different (p<0.001). Only two conditions of stimulation for Donor 2 (LPS and PHA) yielded similar distributions of rates (p=0.8622). These results suggest that distinguishing immune responsiveness with measures of both frequencies and the distribution of the rates may be more robust than single-parameter measures (frequencies).

Simultaneous Detection of Multiple Cytokines from Single Cells

Figure 10A:
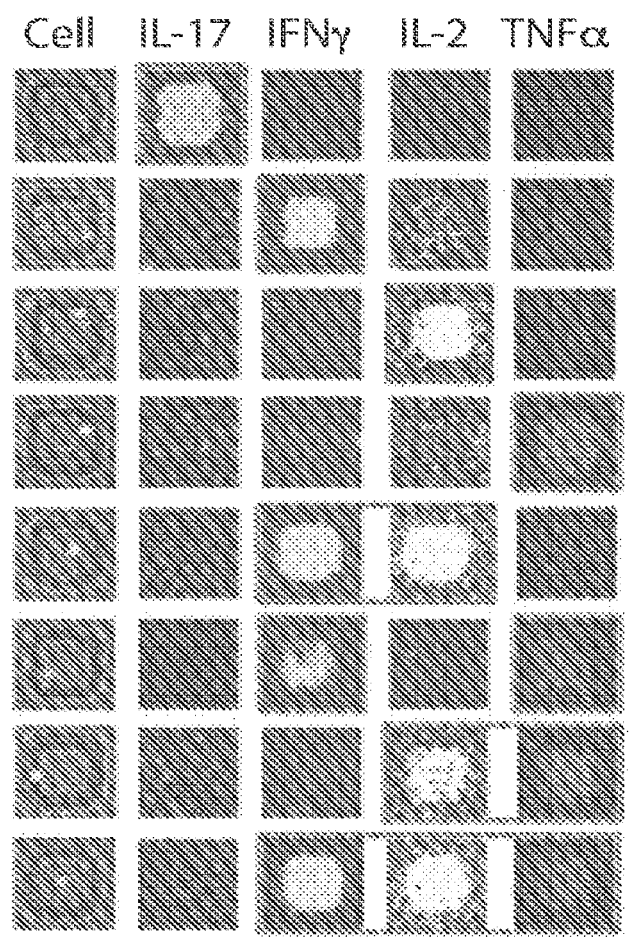
FIG. 10 is a photomicrograph and a series of charts demonstrating quadriplexed analysis of cytokines from single cells. Human PBMCs were stimulated with PMA/ionomycin for 6 h. (A) Representative images of individual cells in microwells matched with micrographs from the corresponding microarray of cytokines (arranged in rows). The first column shows composite micrographs of microwells (phase contrast) and cells (Calcein AM). The remaining four columns are micrographs extracted from the matching location on the printed microarray for each of four cytokines (IL-17, blue; IFNγ, green; IL-2, yellow; TNFα, red). Orange boxes outside the images indicate the positive spots in each row (MFI>background+3σ). (B) Histograms of the rates of secretion for each cytokine organized according to the combinations of cytokines produced. The colors match the assignments in (A). The inset rows of squares in each histogram indicate the combination of cytokines produced by the cells represented in the plot. The values of n in each histogram are the normalized total number of cytokine-producing cells per 100,000 cells. The histograms were constructed with data from three independent experiments.
Figure 10B:
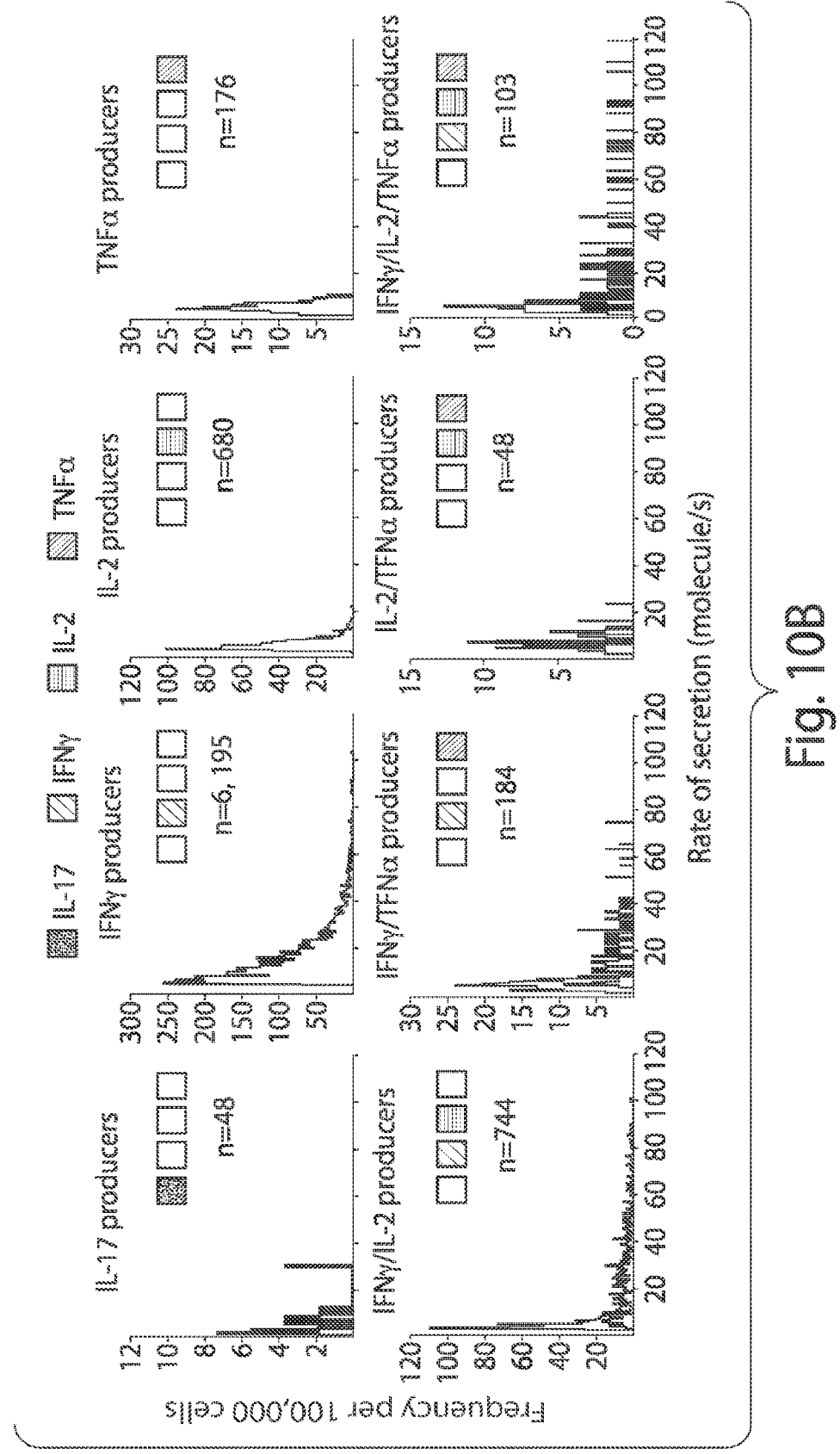
Figure 11:
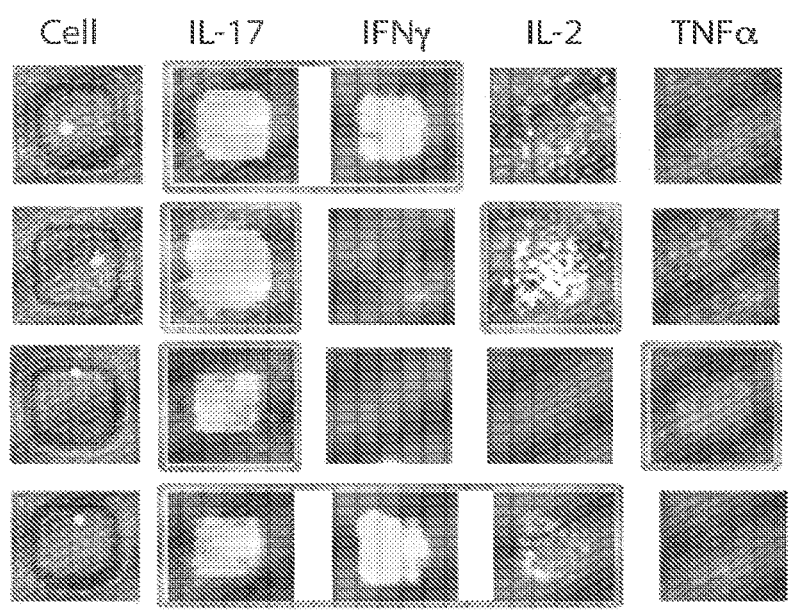
FIG. 11 is a photomicrograph showing representative images of low-frequency functional cells in multiplex detection. The first column shows composite micrographs of microwells (phase contrast) and cells (Calcein AM). The remaining four columns are micrographs extracted from the matching location on the printed microarray for each of four cytokines (IL-17, blue; IFNγ, green; IL-2, yellow; TNFα, red). Orange box outside the images indicate the positive spots in each row (MFI>background+3 SD).
Figure 12A:
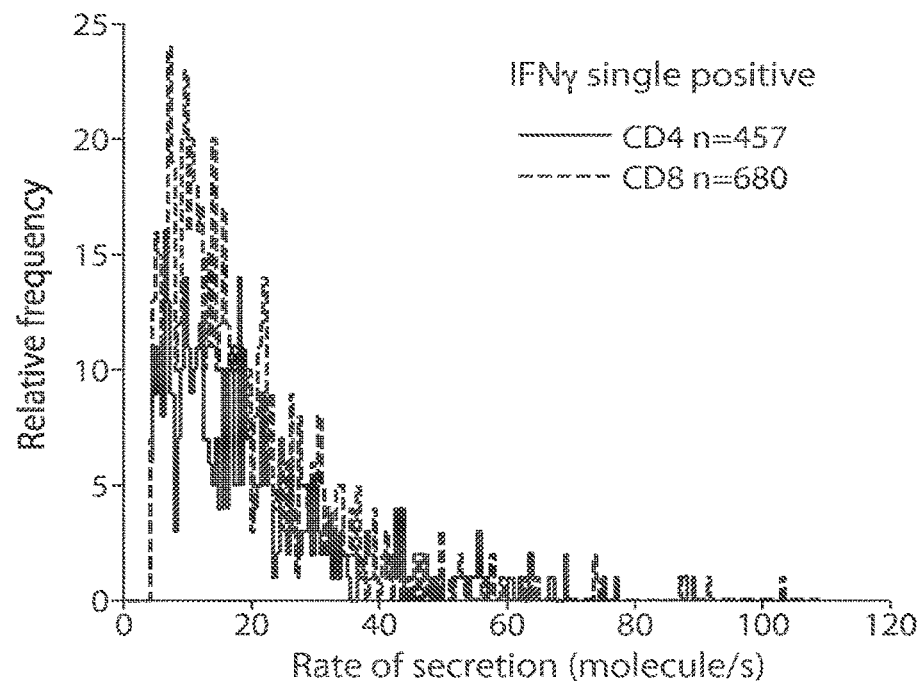
FIG. 12 is a pair of histograms showing the rates of secretion measured for CD4 and CD8 T cells producing (A) IFNγ or (B) IL-2. n is the raw number of cells after microengraving bearing the indicated surface markers. (p=0.055 for IFNγ, p=0.94 for IL-2).
Figure 12B:
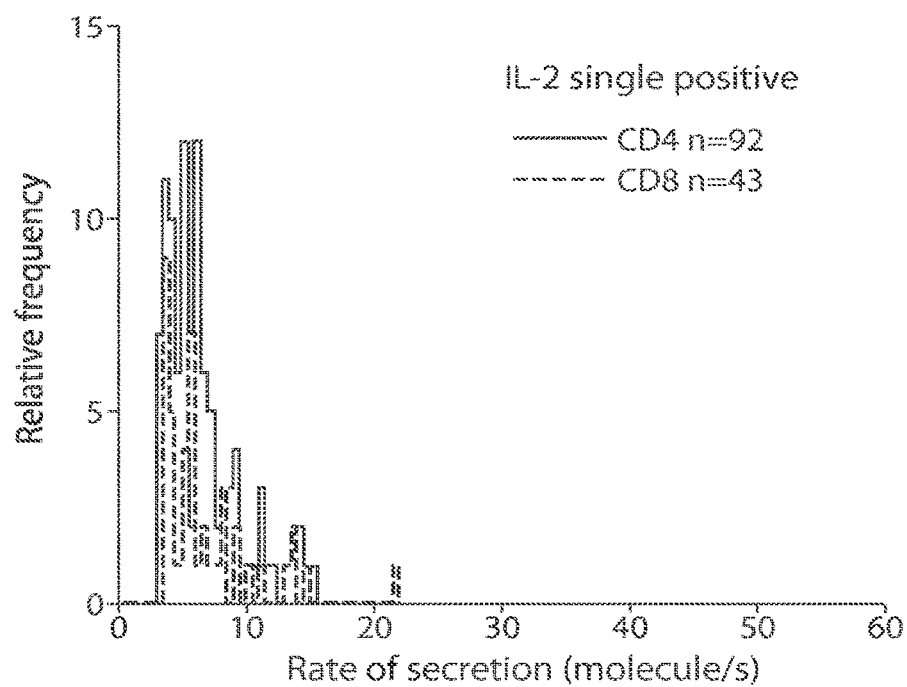

The analytical model for microengraving suggested that multiple cytokines could be detected independently from the same cell, assuming sufficient specificities for each pair of Abs used for capture and detection. Four commercial pairs of Abs were validated to detect simultaneously IL-17, IFNγ, IL-2, and TNFα, and then, measured the breadth of responses in human PBMCs after stimulation with PMA/ionomycin by quantitative microengraving. The live cells in the array exhibited a range of functional responses comprising one, two, or three cytokines (FIG. 10A and FIG. 11). For cells secreting combinations of cytokines (min. 48 per 100,000 cells), the rates of secretion for each cytokine were analyzed (FIG. 10B). The release of IFNγ was the most dynamic (3.8-120 molecule/s), while the rates for other cytokines were typically less than 20 molecule/s. IFNγ and IL-2+ cells included both CD4 and CD8 T cells: Although the frequencies of each lineage differed, the distributions of their rates of secretion were similar (FIG. 12). These data indicate, as expected, that there is no significant difference in the secretory capacities of CD4 and CD8 T cells.

Figure 13A:
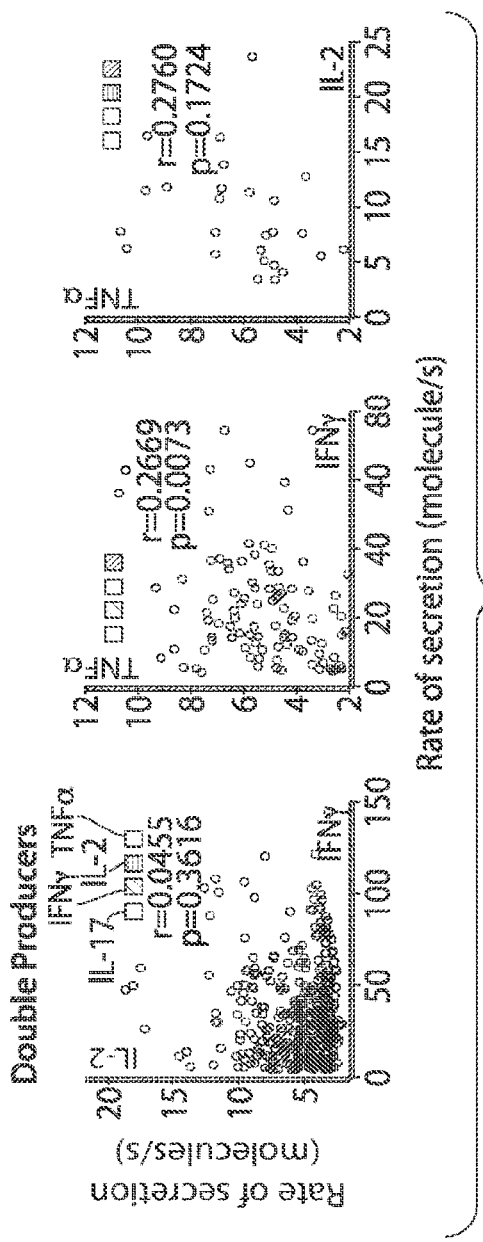
FIG. 13 is a series of graphs demonstrating the correlation of co-secreted cytokines. (A) Two-dimensional scatter plots of the rates of secretion for pairs of cytokines from IFNγ/IL-2, IFNγ/TNFα, and IL-2/TNFα double producers. The color of each axis indicates the type of cytokine in that dimension (IFNγ, green; IL-2, yellow; TNFα, red). Each dot indicates one cell, where the x and y values are the rates of secretion for the pair of cytokines; r is the correlation coefficient, and p is the probability of no correlation. (B) Two-dimensional plots of each pair of cytokines for IFNγ/IL-2/TNFα triple producers. (C) Scatter plots of rates for CD4 (blue) and CD8 (red) IFNγ/IL-2 (upper panel) and IFNγ/TNFα (lower panel) T cells. The number n is the total number of spots in the plots.
Figure 13B:
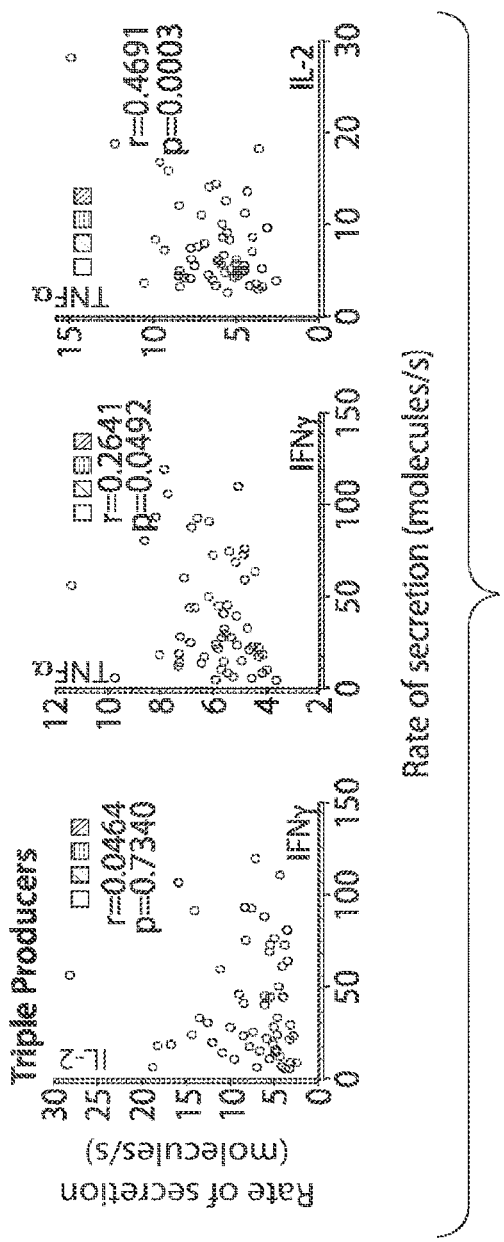
Figure 13C:
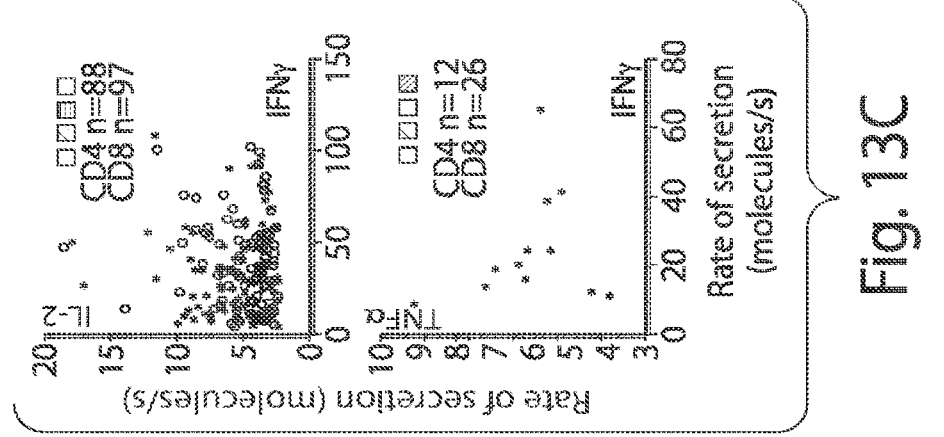

Analysis of multifunctional cells by ICS has indicated that double and triple cytokine-producing cells express greater quantities of cytokines inside the cell than single producers when secretion is blocked (Darrah, et al., 2007 *Nat Med*, 13:843-850). In the experiments, the distribution in the rates of secretion for IFNγ also varied between single producers and double/triple producers (FIG. 10B). The median rate of secretion of IFNγ increased 2.2-fold when cells co-secreted IL-2 or IL-2/TNFα. There was not, however, a distinct difference in the rates of secretion for the other cytokines. The data was further analyzed to determine whether the rates of secretion in double and triple producers correlated for multiple cytokines (FIG. 13A,B). There was a positive correlation between the rates of secretion for IFNγ and TNFα for double producers, and between IFNγ/TNFα and IL-2/TNFα for triple producers. In contrast, the rates of secretion for IFNγ and IL-2 were not correlated for either double or triple producers. These results are consistent with previous studies on the co-expression of cytokines: the genes for IL-2 and TNFα are co-regulated by common transcription factors (Decker, E L 2003 *Nucleic Acids Research*, 31:911-921), while IFNγ and IL-2 are regulated independently (Penix, et al., 1993 *J Exp Med*, 178:1483-1496). That there was no significant difference in the frequencies or correlation of rates between IFNγ+/IL-2+ CD4 and CD8 T cells, while the frequency of IFNγ+/TNFα+CD8 T cells was approximately twofold greater than CD4 T cells (FIG. 13C). These results show that microengraving reveals the subtle dynamics of secretion exhibited by multifunctional cells obscured in ICS.

Described herein is a quantitative method using microengraving to produce multidimensional profiles of the cytokines released from individual viable lymphocytes. The technical advantages of this approach are: 1) it yields a quantitative measure of secretory function that is compared across samples, and 2) the mechanism of mass transport enhances the sensitivity of the method (Table 3) compared to other secretion-based assays (ELISpot, surface capture) by an order of magnitude (Frykman, et al., *Biotechnol Bioeng*, 59:214-226). These characteristics minimize the perturbations to the cells before and during the measurements. Furthermore, assigning rates of secretion to individual cytokines released from single cells increases the dimensionality of analyses for multifunctional cells. Integration of imaging cytometry with these measurements yields a combination of single-cell data that includes the lineage of cells as well as the number and rates of secreted cytokines. Such data improves the differentiation of heterogeneous subsets of cells that are crucial for evaluating vaccine responses and understanding the pathology of chronic diseases, especially when characterizing clinical samples where the number of cells available may be insufficient for analysis by independent conventional methods (e.g., infants, tissue biopsies).

TABLE 3

Experimental limits of detection for five cytokines

| Cytokine | Fluorophore | Limit of detection (molecule/s) |
| --- | --- | --- |
| IL-6 | Alexa Fluor 488 | 0.52-0.67 |
| IL-17 | Alexa Fluor 488 | 0.48-0.63 |
| IFNγ | Alexa Fluor 555 | 3.80-4.11 |
| IL-2 | Alexa Fluor 594 | 0.76-3.10 |
| TNFα | Alexa Fluor 700 | 1.75-2.00 |

The limit of detection was determined for the specific fluorophore used on each detection antibody and defined as three standard deviations (SD) above the average background. These values are at least 10-times lower than those previously calculated for artificial receptor assays, and in most cases, are lower than those for encapsulation assays.

Example 4

Appling Microengraving Technology to Allergy Test and Diagnoses Background on Allergy The cytokine secretion profiles of different kinds of Th cells, as well as the frequencies of different Ig subtype secreting B cells are determined. The information is used to diagnose allergen sensitivity and monitor immunity change during allergy immune therapy.

Three detection chips are developed. They include: Th set: IL-17 ($T_{h17}$), IL-10 ($T_{reg}$), IL-4 ($T_{h2}$), and IFN-g ($T_{h1}$). These are representative cytokines of four subtypes of CD4$^+$ T cells. Th2 set: IL-4, IL-5, IL-13, and IL-9, four important $T_{h2}$ cytokines in allergy. Ab set: IgE, IgG$_1$, IgG$_4$, and IgA, four subtypes of immunoglobulin molecule in allergy process.

Pairs of antibodies suitable for a $T_{h2}$ set are identified, and their standard curves and cross reactions tested.

To measure immunoglobulin secretion, glass slides are functionalized with allergen to capture allergen specific antibodies. Four anti-human Ig isotype antibodies (anti-human IgE, anti-human IgG$_1$, anti-human IgG$_4$, and anti-human IgA) are used as detection antibodies. Human IgE, IgG$_1$, IgG$_4$, and IgA standards are used to test the specificity of commercialized anti-human Ig isotype antibodies.

The antibody chip aims to measure four different Ig isotypes in single assay. However, immunity of allergen peptides may be lost or weakened when directly coating allergen on the glass surface. Alternatively, each kind of anti-human Ig antibody is used as capture antibody on four different slides. Allergen is fluorescently labeled and used as detection reagent.

The peanut allergy model is used to study the cell reaction upon peanut treatment. Blood samples from subjects with peanut allergy and subjects without peanut allergy are obtained. PBMCs are isolated from each blood sample and stimulated with the same peanut extract as used in clinical diagnosis. The response of PBMCs is examined using Th, Th2, and Ab chips. A time course study, together with an allergen gradient, is performed to determine the best in vitro stimulation condition. Cytokine profiles and frequencies of allergen specific immunoglobulins of subjects with peanut allergy are statistically analyzed and compared to profiles from subject without peanut allergy. Significant differences between these two populations are considered diagnostic of an allergy. Optionally, the cytokine profile and Ig secretion at different disease stages or during treatment are examined to study the changes of the immune system during allergy development and to explore the potential application of microengraving on clinical test.

The expansion of microengraving technology developed herein enables highly efficient multiplexed analysis of single cells, especially in the field of immunological study. The signature of single cells helps better understand the network of immune cells and dynamically trace the changes of cell behaviors during disease development. The low cost of the materials, standard process, and short operation time of this technology also provide the opportunity in clinical diagnosis. Besides allergy study, the extension of this method can also be used in autoimmune and infectious diseases.

Other Embodiments

Figure 14:
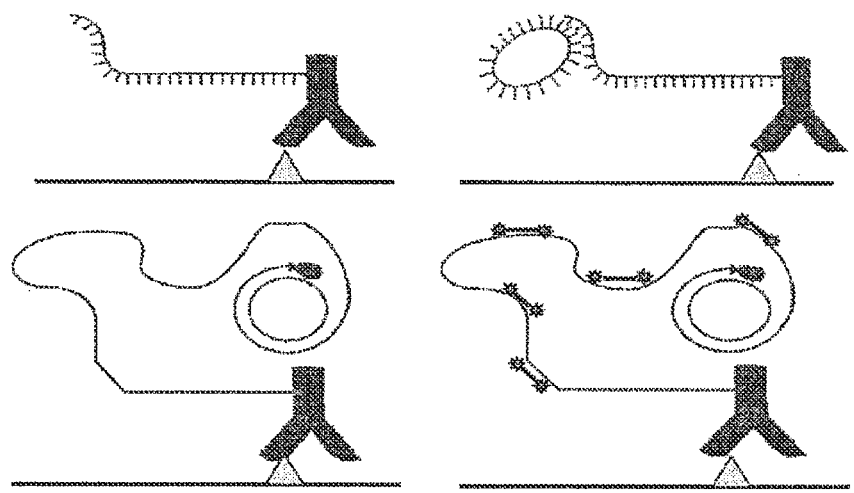
FIG. 14 is an illustration of the mechanism of rolling circle amplification. Detection antibody is conjugated to an oligonucleotide. A DNA circle hybridizes to a complementary sequence in the oligonucleotide and amplified through polymerase chain reaction (PCR). Finally, the amplified DNA sequence is labeled in situ by hybridization with fluorescence-labeled oligonucleotides.
Figure 15:
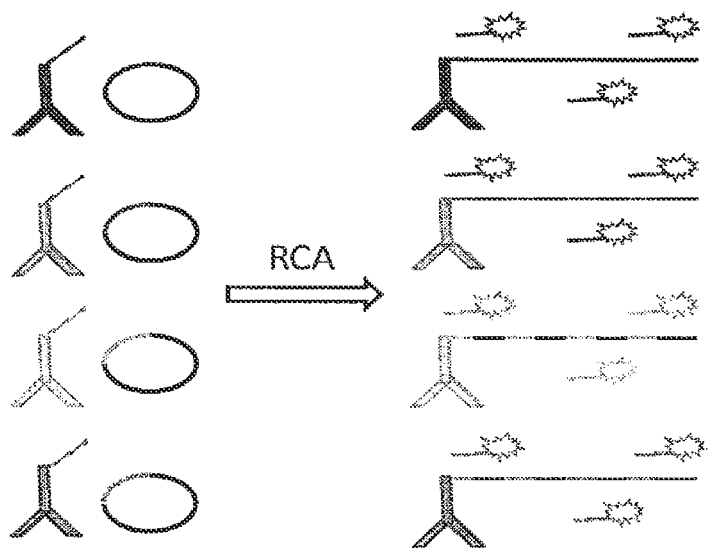
FIG. 15 is an illustration of the design of multiple cytokine detection using rolling circle amplification (RCA). Each kind of detection antibody is linked with a unique oligonucleotide sequence. Four circling DNA with complementary sequence to primers are used to amplify the primers. Four reporter sequences are labeled with different fluorophores to hybridize the long DNA chains.

Increasing the Cytokine Detection Sensitivity and Expanding the Number of Cytokines Per Assay To increase the sensitivity of the assay, rolling circle amplification (RCA) (Schweitzer, et al., 2002 *Nat Biotechnol*, 20: 359-365) is used to detect multiple cytokines per assay. An advantage of RCA is that it converts a single signal from an antibody into anamplifiable DNA molecule (FIG. 14). Instead of labeling detection antibodies with different fluorescent colors, detection antibodies are labeled with different primers (FIG. 15). The circular DNA is constructed with two parts. One part is a conserved sequence, which is the same in all the circular DNA. Another part is complementary to the specific primer bound to the detection antibody for each cytokine.

After applying the detection antibody, circular DNA is added into the system and amplified through certain cycles, where the primers attached to the detection antibodies are elongated. In the end, reaction reagents are removed, and reporter sequences with fluorophores are added.

The number of cytokines that are detected per assay also depends on the fluorescent colors available and excitation laser and filters in the instrument. Currently, GenePix scanner is used and has four lasers: 488 nm, 532 nm, 594 nm, and 635 nm. With the standard filters, four colors are detected from the instrument. However, with the combination of other additional filters, two or three other colors using fluorophore such as Alexa Fluor 700, Alexa Fluor 750, or Qdot can be added.

Figure 16:
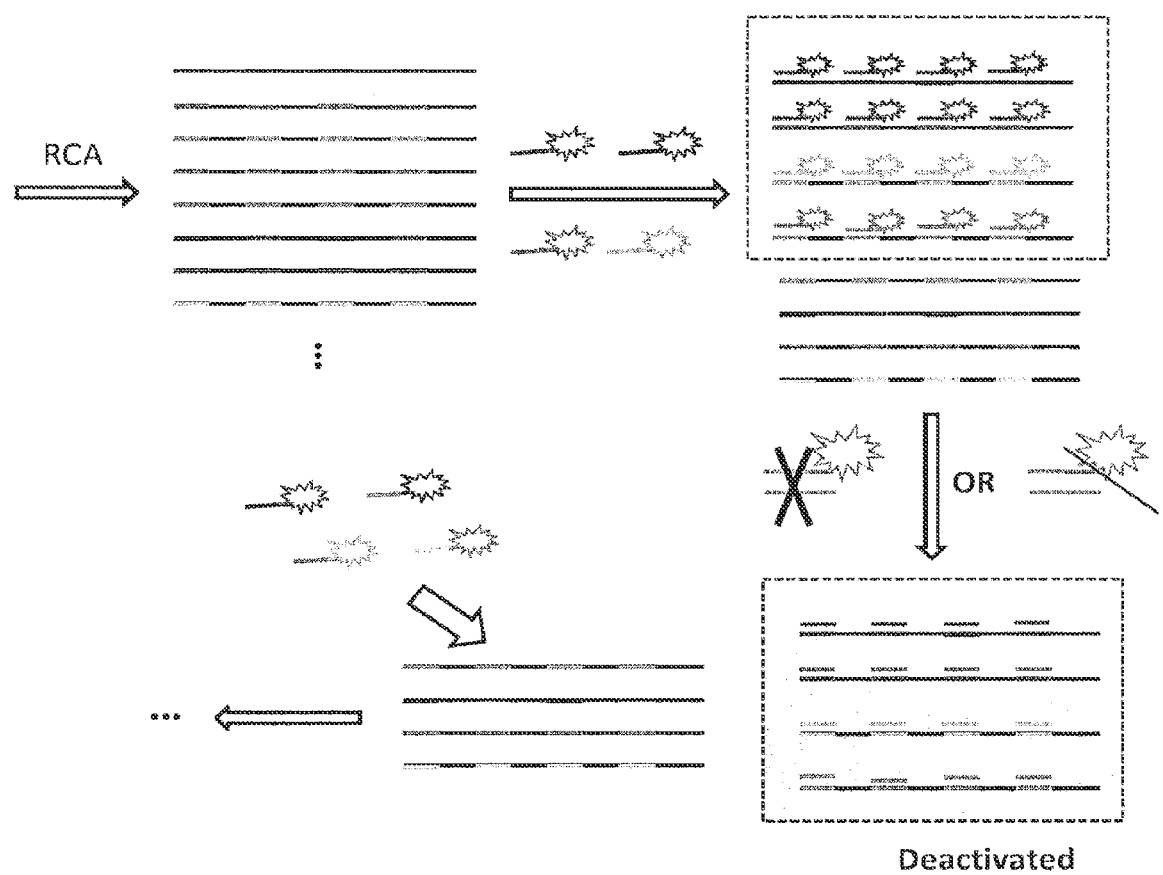
FIG. 16 is a diagram showing the design of sequential labeling based on RCA for multiple cytokine detection. After RCA process as shown above, the first set of reporter sequences with fluorescent labeling are added in the system to detect corresponding sequences. After scanning, the slides were either treated with enzyme to specifically cleave double strand DNA or with chemical reagent to cleave the linker between reporter sequence and fluorophore. After this process, the amplified sequences for the first set of cytokines are deactivated. Then, the second set of reporter sequences with fluorophore is applied on the system to detect another set of cytokines. The whole detection process can be repeated several times.
Figures 2, 17:
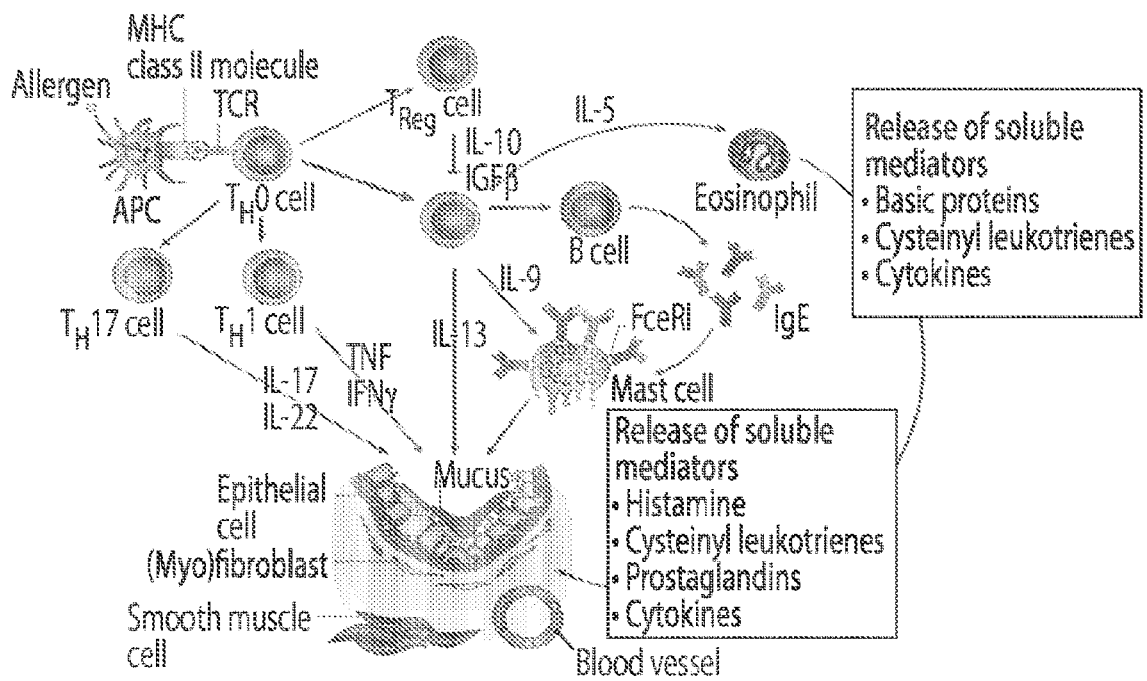
FIG. 17 is a series of illustrations illustrating the problem with current allergy testing.
Figure 18C:
FIG. 18 is a series of illustrations and graphs demonstrating implementation of the microengraving method described herein. Panel A presents a schematic of a described microengraving method. Panel B provides points relating to how the method illustrated in Panel A works. Panels C and D present exemplary data obtained.
Figure 18D:
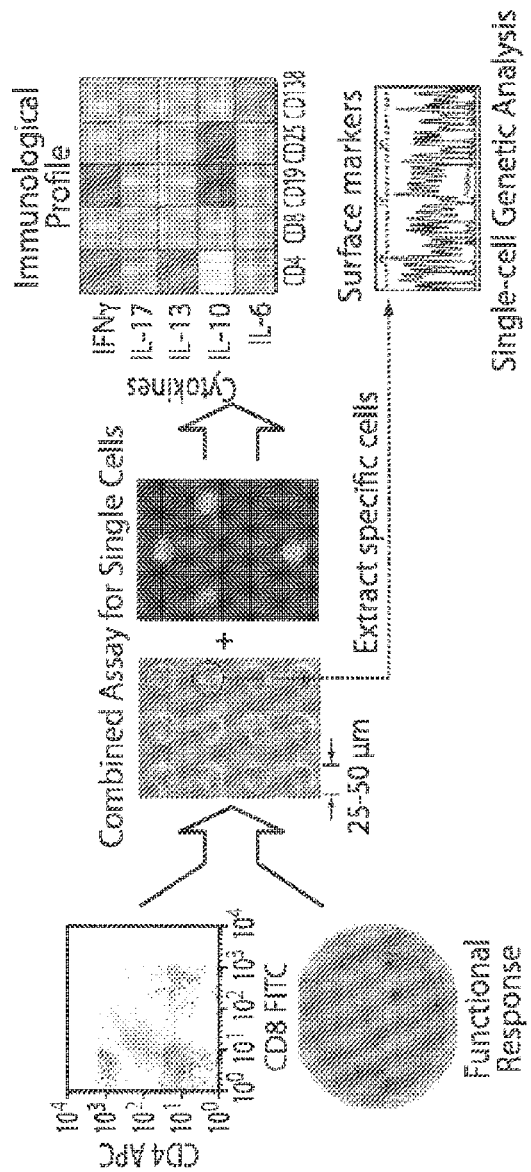
Figure 19C:
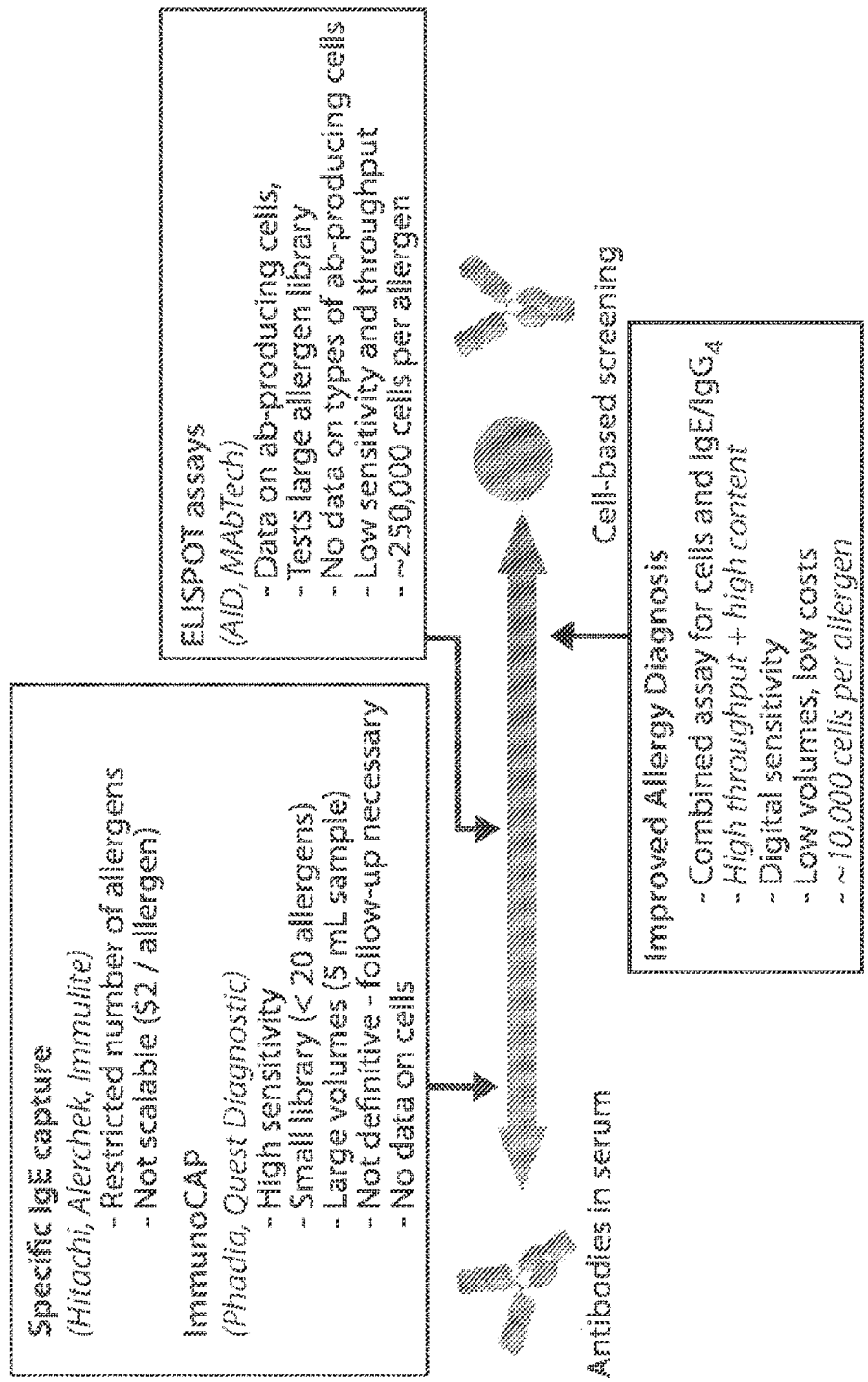
FIG. 19 is a series of illustrations profiling the allergic response. Panel A presents a schematic of steps in a provided method for profiling an allergic response. Panel B provides bullet point descriptions of steps in such a provided method. Panel C provides an illustration comparing such a provided method with certain other methodologies, and highlights particular advantages.

However, in order to decrease the overlap of different fluorescence spectra, the space for the fluorescent colors is limited. With the advantage of the higher diversity of DNA sequences, a sequential labeling strategy to expand the number of cytokines is designed based on the RCA. As shown in FIG. 16, after the RCA reaction, signals are detected group by group, depending on the color available per scanning. For example, four reporter sequences with different colors are added to detect the first four cytokines. After scanning, the first set of fluorescent molecules are removed from the slides. One method is to cut the double stranded DNA portion, which will remove the detected sequences from the system. Another method is to use a cleavable linker between the reporter DNA and the fluorophore, so that fluorophore can be cleaved after detection (Ju, et al., 2006 *Proc Natl Acad Sci USA*, 103: 19635-19640). After washing away the fluorescent molecules in the system, the second set of reporters are applied on the system to hybridize another set of DNA sequences. Because the first set of fluorophores has been removed, the second set of reporter sequences are labeled with the same colors.

RCA is performed first on single cytokine detection in a microengraving system. Circular DNA and primer sequence as published by Schweitzer et al. are used (Schweitzer et al., 2002 *Nat Biotechnol*, 20: 359-365).

Circle:
5'-CTC AGC TGT GTA ACA ACA TGA AGA TTG TAG GTC

AGA ACT CAC CTG TTA GAA ACT GTG AAG ATC GCT TAT

TAT GTC CTA TC-3'

Primer:
5'-CAC AGC TGA GGA TAG GAC AT-3'

Reporter:
5'-ATG TCC TAT CCT CAG CTG TG-3'

The two temperatures used in the amplification process are 45° C. and 37° C. This amplification step is integrated and performed by washing machine so that all the steps after printing are automatically performed. One cytokine is used initially to optimize the process (reaction concentration and time) and determine the detection sensitivity.

Using the same cytokine model developed above, two methods are used to remove the fluorophore after detection: 1) A cleavable linker to is used to conjugate fluorophore to the reporter DNA. One choice is a photocleavable 2-nitrobenzyle linker, which can be cleaved using laser irradiation (355 nm) in 10 sec (Seo, et al., 2005 *Proc Natl Acad Sci USA*, 102: 5926-5931). Another choice is allyl group linker, which can be removed in 30 seconds by Pd-catalyzed (Ju, et al., 2006 *Proc Natl Acad Sci USA*, 103: 19635-19640; Bi, et al., 2006 *J Am Chem Soc*, 128: 2542-2543). 2) An endonuclease is used to digest double strand DNA. The priority is to find non sequence specific endonuclease to cleave the reporter bound DNA portion. If an endonuclease is unavailable or too expensive, a sequence specific restriction endonuclease is used. In this case, the cleavage site is considered in the design of primer, circling DNA, and reporter. The efficacy of fluorophore-removal is evaluated across all the above methods and the best strategy are used in the following steps.

Circling DNA for multiple cytokine detection is designed and applied to multiple cytokine detection using sequential labeling. Another three sets of primer, circling DNA, and reporter is designed based on the first set of sequences shown above. The general strategy is to change the sequences of primer, reporter, and the portion of circling DNA that is complementary to the primer, while keeping other part of the circling DNA unchanged (as shown in FIG. 15). Four fluorophores are conjugated to four reporters, respectively. Four primers are conjugated to four detection antibodies. The same fluorophores and antibody sets used in preliminary study are used in this step. In the detection step, four reporters are added at the same time to measure the sensitivity of multiple-cytokine detection. Sequential labeling is tested by adding each reporter at different time and removed after scanning. The aim is to measure the maximal repeat of detections that can be used in our system. In addition, another four or eight primers are designed to expand the total number of cytokines to eight or twelve per assay.

In some embodiments, the steps described above are implemented in computer programs using standard programming techniques. Such programs are designed to execute on programmable computers each including an electronic processor, a data storage system (including memory and/or storage elements), at least one input device, and least one output device, such as a display or printer. In some embodiments, the code is applied to the acquired data (e.g., cytokine binding data), to perform the functions described herein, and to generate output information (e.g., assessing allergy status), which is applied to one or more output devices. Each such computer program can be implemented in a high-level procedural or object-oriented programming language, or an assembly or machine language. Furthermore, the language can be a compiled or interpreted language. Each such computer program can be stored on a computer readable storage medium (e.g., CD ROM or magnetic diskette) that when read by a computer can cause the processor in the computer to perform the analysis described herein.

In operation, referring to FIG. 21, a process 30 for calculating immune profile (38) and providing clinical diagnosis (40) includes determining cell type (32), determining magnitude of secretion (34), and determining frequency of responders (36).

Table 4 shows the phenotypic profile of Th1, Th2, and Th-17 cell types.

TABLE 4

Phenotypic Profile of Th1, Th2 & Th-17 Cell Types

| | Cell Type: | | |
|---|---|---|---|
| | Th1 | Th2 | Th-17 |
| Surface Phenotype: | | | |
| CD3 | + | + | + |
| CD4 | + | + | + |
| IFN-γR | + | | |
| IL-12Rβ2 | +upregulated by IFN-γ | − | + |
| IL-23R | | + | +downregulated by IFN-γ |
| Tim-3 | + | − | ? |
| Cytokine Profile: | | | |
| IFN-γ | + | − | − |
| IL-2 | + | +/− | − |
| IL-4 | − | + | − |
| IL-5 | − | + | − |
| IL-6 | | +/− | + |
| IL-10 | − | +(m) | − |
| IL-12 | − | − | − |
| IL-13 | − | + | − |
| IL-17A | − | − | + |
| IL-17F | − | − | + |
| IL-22 | − | − | + |
| IL-25 | − | + | − |
| IL-31 | − | + | − |
| IL-33 | − | + | − |
| TNF-α | + | − | + |

Additional embodiments are within the claims.

What is claimed is:

1. A method of measuring a dynamic change in a profile of viable T cells, comprising:
   performing a first contacting step at a first time point, wherein the first contacting step comprises contacting a slab with a first substrate,
   wherein the slab contains an array of microwells, each microwell dimensioned to hold a subnanoliter volume of liquid, wherein microwells in the array of microwells contain viable T cells and products secreted from said T cells, and, on average, contain no more than one single T cell or a few T cells per microwell;
   wherein the first substrate is pretreated with a plurality of first detection agents, wherein said plurality of first detection agents comprises first detection agents that respectively bind to different cytokines, whereby cytokines secreted by said T cells that are present in said microwells and are binding partners of a first detection agent are bound to the first detection agent in regions on the first substrate contacted by contents of the microwells, to yield a first printed array;
   after step (a), performing a second contacting step at a second time point, which second contacting step comprises contacting the slab with a second substrate, wherein the second substrate is pretreated with a plurality of second detection agents, wherein said plurality of second detection agents comprises second detection agents that are identical to said first detection agents that respectively bind to different cytokines, whereby cytokines secreted by said T cells that are present in said microwells and are binding partners of a second detection agent are bound to the second detection agent in regions on the second substrate contacted by contents of the microwells, to yield a second printed array;
   quantifying levels of said different cytokines bound to the first printed array and levels of said different cytokines bound to the second printed array, and
   determining rates of secretion of the different cytokines bound to the first printed array and rates of secretion of the different cytokines bound to the second printed array, thereby measuring a dynamic change in a profile of the T cells.

2. The method of claim 1, wherein the different cytokines are T-helper 1 ("Th$_1$") cytokines, T-helper 2 ("Th$_2$") cytokines, T-helper 9 ("Th$_9$") cytokines, T-helper 17 ("Th$_{17}$") cytokines, or T-helper ("Th") cytokines.

3. The method of claim 2 which further comprises, for a plurality of locations in the array of microwells that contain only a single cell, matching each location with data extracted from the first printed array and data extracted from the second printed array in a region contacted by contents of the microwell at the location, wherein the data represents the level bound in said region of a selected cytokine included within said different cytokines; and repeating said matching for each cytokine included within said different cytokines.

4. The method of claim 1, wherein the different cytokines are selected from the group consisting of IL-17, IL-10, IL-4, and IFN-γ.

5. The method of claim 1, wherein the different cytokines are Th cytokines.

6. The method of claim 1, wherein the different cytokines are selected from the group consisting of IL-4, IL-5, IL-13, and IL-9.

7. The method of claim 1, wherein the different cytokines are cytotoxic T lymphocyte (CTL) or Th$_1$ cytokines.

8. The method of claim 1, wherein the different cytokines are selected from the group consisting of IFNγ, MIP-1β, TNFα, perforin, and IL-2.

9. The method of claim 1, which further comprises stimulating the T cells and depositing the stimulated T cells in the microwells prior to step (a).

10. The method of claim 1, wherein the T cells are stimulated with a suspected or known allergen.

11. The method of claim 10, wherein the allergen is a food product.

12. The method of claim 11, wherein the food product is milk, egg, peanut, tree nut, fish, shellfish, soy, wheat, an egg product, a legume, seafood or shellfish.

13. The method of claim 10, wherein the allergen is a drug.

14. The method of claim 13, wherein the drug is amoxicillin, penicillin, a sulfa drug, a barbiturate, an anticonvulsant, insulin, or iodine.

15. The method of claim 10, wherein the allergen is dust, pollen, pet dander, latex, chlorine, or venom associated with an insect bite.

16. The method of claim 10, wherein the allergen is from a wasp, fire ant or bee sting.

17. The method of claim 10, wherein the T cells are from a subject, and an increase in the level of a $Th_e$ cytokine compared to a level of a $Th_1$ cytokine indicates that the subject is allergic or is at risk of developing an allergy to the allergen.

18. The method of claim 17, wherein the $Th_2$ cytokine comprises IL-4.

19. The method of claim 17, wherein the $Th_1$ cytokine comprises IFNγ.

20. The method of claim 1, further comprising determining the phenotype or lineage of the T cells.

21. The method of claim 20, further matching the phenotype or lineage with the levels of said different cytokines bound to the first printed array and the levels of said different cytokines bound to the second printed array.

22. The method of claim 1, wherein the step of quantifying comprises imaging each of the first printed array and the second printed array to yield a dataset; filtering the dataset to identify locations on the array of microwells in which the microwells contain a single cell; and matching the locations of the microwells with the corresponding locations on the first printed array and the second printed array and with levels of said different cytokines detected from the locations.

23. The method of claim 1, wherein the T cells are from a subject, and the dynamic change in the profile of the T cells is indicative of an autoimmune disease or infectious disease in the subject.

24. The method of claim 1 wherein said first detection agents that respectively bind to different cytokines are capture antibodies that respectively bind to said different cytokines, and said quantifying step comprises contacting the first printed array and second printed array with detection antibodies that respectively bind to said different cytokines.

25. The method of claim 24 wherein the detection antibodies that respectively bind to said different cytokines are labeled with different fluorescent labels.

26. The method of claim 25 wherein the T cells are human T cells, the different cytokines comprise IFNγ, IL-2, and TNFα, and the method further comprises one or more additional contacting steps after step (b), wherein each additional contacting step: (i) is at a different time point, and (ii) comprises contacting the slab with an additional substrate, wherein the additional substrate is pretreated with a plurality of additional detection agents that comprise additional detection agents identical to said first detection agents that respectively bind to different cytokines, whereby cytokines secreted by said T cells that are present in said microwells and are binding partners of an additional detection agent are bound to the additional detection agent in regions on the additional substrate contacted by contents of the microwells, to yield an additional printed array; and wherein said quantifying step further comprises quantifying levels of said different cytokines bound to each said additional printed array, and determining rates of secretion of the different cytokines bound to each said additional printed array.

27. The method of claim 25 which further comprises, for a plurality of locations in the array of microwells that contain only a single cell, matching each location with data extracted from the first printed array and data extracted from the second printed array in a region contacted by contents of the microwell at the location, wherein the data represents the level bound in said region of a selected cytokine included within said different cytokines; and repeating said matching for each cytokine included within said different cytokines.

28. The method of claim 1 wherein said different cytokines are up to four different cytokines.

29. The method of claim 1 wherein the T cells are human T cells.

30. The method of claim 29 wherein the different cytokines comprise IFNγ, IL-2, and TNFα.

31. The method of claim 30 which further comprises, for a plurality of locations in the array of microwells that contain only a single cell, matching each location with data extracted from the first printed array and data extracted from the second printed array in a region contacted by contents of the microwell at the location, wherein the data represents the level bound in said region of a selected cytokine included within said different cytokines; and repeating said matching for each cytokine included within said different cytokines.

32. The method of claim 1 further comprising one or more additional contacting steps after step (b), wherein each additional contacting step: (i) is at a different time point, and (ii) comprises contacting the slab with an additional substrate, wherein the additional substrate is pretreated with a plurality of additional detection agents that comprise additional detection agents identical to said first detection agents that respectively bind to different cytokines, whereby cytokines secreted by said T cells that are present in said microwells and are binding partners of an additional detection agent are bound to the additional detection agent in regions on the additional substrate contacted by contents of the microwells, to yield an additional printed array; and wherein said quantifying step further comprises quantifying levels of said different cytokines bound to each said additional printed array, and determining rates of secretion of the different cytokines bound to each said additional printed array.

33. The method of claim 32 which further comprises, for a plurality of locations in the array of microwells that contain only a single cell, matching each location with data extracted from the first printed array, data extracted from the second printed array, and data extracted from each said additional printed array, in a region contacted by contents of the microwell at the location, wherein the data represents the level bound in said region of a selected cytokine included within said different cytokines; and repeating said matching for each cytokine included within said different cytokines.

34. The method of claim 1 which further comprises, for a plurality of locations in the array of microwells that contain only a single cell, matching each location with data extracted from the first printed array and data extracted from the second printed array in a region contacted by contents of the microwell at the location, wherein the data represents the level bound in said region of a selected cytokine included within said different cytokines; and repeating said matching for each cytokine included within said different cytokines.

* * * * *

UNITED STATES PATENT AND TRADEMARK OFFICE
CERTIFICATE OF CORRECTION

PATENT NO. : 9,244,080 B2
APPLICATION NO. : 13/132858
DATED : January 26, 2016
INVENTOR(S) : J. Christopher Love et al.

Page 1 of 1

It is certified that error appears in the above-identified patent and that said Letters Patent is hereby corrected as shown below:

Claims

Please correct Column 26, Line 47-48, claim 5 from:

"The method of claim 1, wherein the different cytokines are The cytokines."

to read:

-- The method of claim 1, wherein the different cytokines are $Th_2$ cytokines. --

Please correct Column 27, Line 9-12, claim 17 from:

"The method of claim 10, wherein the T cells are from a subject, and an increase in the level of a $Th_e$ cytokine compared to a level of a $Th_1$ cytokine indicates that the subject is allergic or is at risk of developing an allergy to the allergen."

to read:

-- The method of claim 10, wherein the T cells are from a subject, and an increase in the level of a $Th_2$ cytokine compared to a level of a $Th_1$ cytokine indicates that the subject is allergic or is at risk of developing an allergy to the allergen. --

Signed and Sealed this
Twenty-sixth Day of April, 2016

Michelle K. Lee
*Director of the United States Patent and Trademark Office*